(12) United States Patent
Laughlin et al.

(10) Patent No.: US 11,911,408 B2
(45) Date of Patent: Feb. 27, 2024

(54) SYNERGISTIC FORMULATIONS OF ADENOSINE RECEPTOR MODULATING AGENTS AND ANTICHOLINERGICS

(71) Applicant: UNIVERSITY OF ALASKA FAIRBANKS, Fairbanks, AK (US)

(72) Inventors: Bernard Laughlin, Fairbanks, AK (US); Kelly Drew, Fairbanks, AK (US)

(73) Assignee: UNIVERSITY OF ALASKA FAIRBANKS, Fairbanks, AK (US)

( * ) Notice: Subject to any disclaimer, the term of this patent is extended or adjusted under 35 U.S.C. 154(b) by 0 days.

(21) Appl. No.: 17/692,383

(22) Filed: Mar. 11, 2022

(65) Prior Publication Data

US 2022/0288099 A1   Sep. 15, 2022

Related U.S. Application Data

(60) Provisional application No. 63/160,356, filed on Mar. 12, 2021.

(51) Int. Cl.
| | | |
|---|---|---|
| A01N 43/04 | (2006.01) | |
| A61K 31/70 | (2006.01) | |
| A61K 31/7076 | (2006.01) | |
| A61K 45/06 | (2006.01) | |
| A61P 9/02 | (2006.01) | |

(52) U.S. Cl.
CPC .......... *A61K 31/7076* (2013.01); *A61K 45/06* (2013.01); *A61P 9/02* (2018.01)

(58) Field of Classification Search
None
See application file for complete search history.

(56) References Cited

PUBLICATIONS

Laughlin, Bernard W., et al. "Reversal of Peripheral and CNS Mediated A1 Adenosine Receptor Hypotension." The FASEB Journal 32 (2018): lb103-lb103.*

* cited by examiner

*Primary Examiner* — Patrick T Lewis
(74) *Attorney, Agent, or Firm* — Barnes & Thornburg LLP

(57) ABSTRACT

The present disclosure provides a pharmaceutical composition comprising i) an A1 adenosine receptor (A1AR) agonist, ii) an A1AR antagonist, and iii) an anticholinergic. Kits utilizing i) an A1 adenosine receptor (A1AR) agonist, ii) an A1AR antagonist, and iii) an anticholinergic are also provided, as well as methods utilizing the described pharmaceutical compositions and kits.

14 Claims, 13 Drawing Sheets

SYNERGISTIC FORMULATIONS OF ADENOSINE RECEPTOR MODULATING AGENTS AND ANTICHOLINERGICS

CROSS-REFERENCE TO RELATED APPLICATIONS

This application claims the benefit under 35 USC § 119(e) of U.S. Provisional Application Ser. No. 63/160,356, filed on Mar. 12, 2021, the entire disclosure of which, including all appendices, is incorporated herein by reference.

GOVERNMENT SUPPORT STATEMENT

This invention was made with government support under 1R41HL135964-01A1 awarded by the National Institutes of Health. The government has certain rights in the invention.

SUMMARY

Adenosine is a purine regulator of metabolism and its main physiological effect is to reduce cellular energy utilization. In the brain, adenosine can decrease neuronal firing rates and release of excitatory neurotransmitters. Adenosine is also a well-known vasodilator and has negative inotropic, chronotropic, and dromotropic influence on the heart. Further, adenosine is a catabolic byproduct of ATP de-phosphorylation and also is a neuromodulator.

There are four known adenosine receptor subtypes: A1AR, $A2_AAR$, $A2_BAR$, and A3AR. All of these receptors are G-protein coupled receptors, in which the A1AR and A3AR subtypes are inhibitory and the A2AR subtypes are stimulatory.

A1 adenosine receptor (A1AR) agonists have numerous therapeutic benefits but are generally undeveloped as therapeutic agents because of undesirable side effects. For example, lowering of metabolic rate decreases tissue demand for blood flow and glucose and oxygen delivery and is expected to be beneficial for a number of clinical scenarios.

A1AR agonists can improve survival and neurological outcomes after cardiac arrest and stroke in animal models and may also be used to inhibit cold-induced metabolic response. In critical care medicine, patients are exposed to cold during targeted temperature management, now the general standard of care following cardiac arrest. Exposure to cold stimulates metabolism and interferes with the therapeutic efficacy of targeted temperature management.

Although A1AR agonists have numerous benefits, their use is limited by peripheral side effects. Systemic activation of A1AR induces a centrally mediated hypometabolic state and notably decreases cardiac output through reduction of heart rate and hypotension. Unchecked hypotension results in multiorgan failure and death. The present disclosure shows that A1AR agonists block metabolic stimulation when a body is exposed to cold, such as during targeted temperature management.

For instance, N6-Cyclohexyladenosine (CHA) is a selective Adenosine A1 receptor agonist. Hypotension observed after treatment with CHA is due in part to activation of A1AR outside of the CNS (Peripheral receptors). As shown in FIG. 1, CHA-induced hypotension can be characterized in three different phases where the first phase immediately following CHA administration is due in part to increased parasympathetic tone to the heat.

It has been demonstrated that administration of adenosine receptor antagonists can help to mitigate the side effects of A1AR agonists. For example, 8-(p Sulfophenyl) theophylline (8-SPT) is a nonselective adenosine receptor antagonist that does not cross the blood brain barrier. However, pretreatment with 8-SPT alone cannot prevent the development of hypotension immediately following CHA administration.

In addition to being an A1AR antagonist, 8-SPT belongs to the class of drugs known as methylxanthines. Methylxanthines are known to increase resting energy expenditure. Undesirably, one complication of administering 8-SPT along with A1AR agonists is the negating effect of 8-SPT on the suppression of metabolism. Further development of A1AR modulating agents requires addressing all phases of hypotension as well as prevention of stimulation of metabolism. Thus, there exists a need for additional pharmaceutical formulations for this therapeutic area.

Accordingly, the present disclosure provides pharmaceutical formulations including i) an A1 adenosine receptor (A1AR) agonist, ii) an A1AR antagonist, and iii) an anticholinergic. The combination of an A1 adenosine receptor agonist with a peripherally acting adenosine receptor antagonist and, further, with an anticholinergic agent provides unexpected synergistic effects that provide a unique mechanism for the therapeutic actions of A1 adenosine receptor agonists.

The present disclosure demonstrates the unexpected synergy between an A1AR agonist (e.g., CHA), a peripherally acting adenosine receptor antagonist (e.g., 8-SPT) and a muscarinic cholinergic antagonist (e.g., atropine or glycopyrrolate) to suppress metabolism without concomitant hypotension. Hypotension is both centrally and peripherally mediated, where others have shown that peripherally mediated hypotension can be prevented with the A1AR antagonist 8-(p-sulfophenyl) theophylline (8-SPT). Unexpectedly, 8-SPT alone is not sufficient to prevent the initial centrally mediated drop in blood pressure or heart rate following CHA systemic administration.

The pharmaceutical formulations provided by the present disclosure provides several advantages that were unexpected compared to the state of the art. A combination of the three drug classes in the described pharmaceutical formulations show synergy in their effects on metabolic rate, heart rate, and blood pressure. Synergy between the therapeutic agents is instructive for means to combine the drugs to realize optimal therapeutic effects.

The present disclosure relates to more precise control of metabolic rate and more precise control of core body temperature. In particular, the described pharmaceutical formulations prevent A1 adenosine receptor mediated hypotension and bradycardia while still effectively inducing metabolic depression in a patient, for example during cold exposure. This may be in the treatment of ischemic reperfusion injury, for targeted temperature management, as an anticonvulsant, neuroprotectant, or other condition treated by activating CNS A1 adenosine receptors. Moreover, rats treated with targeted temperature management utilizing the pharmaceutical formulations were observed to have increased survival rates after cardiac arrest compared to the current standard of care drug combination of meperidine and buspirone.

The synergism observed by utilizing pharmaceutical formulations including i) an A1 adenosine receptor (A1AR) agonist, ii) an A1AR antagonist, and iii) an anticholinergic was unexpected. For instance, synergism exists between an adenosine receptor antagonist and an antimuscarinic to block both centrally and peripherally mediated hypotension caused by an A1AR agonist. Synergy was also observed between an A1AR antagonist and an anticholinergic to block both centrally and peripherally mediated hypotension caused by an A1AR agonist. As described herein, these effects were synergistic and unexpected.

BRIEF DESCRIPTIONS OF THE DRAWINGS

The detailed description particularly refers to the accompanying figures in which:

FIG. 1 is a schematic of the three phases of CHA induced hypotension. Phase I represents the immediate drop in blood pressure after A1AR agonist administration. Phase II represents the recovery period where blood pressure attempts to return to baseline. Phase III represents the maximum A1AR mediated repression of blood pressure obtained after recovery. Two mechanisms are responsible for A1AR mediated hypotension. The initial fall in hypotension (Phase I) is likely centrally mediated primarily through increased endogenous parasympathetic tone to the heart and direct A1AR effect on the heart. Recovery in phase II is likely mediated through the baroreflex response. Repressed baseline pressure in phase III is likely attributed to the direct binding of A1AR on the heart.

FIG. 2 shows synergism between atropine and 8-SPT to reverse effects of CHA is evident for mean arterial pressure (MAP), heart rate (HR), Systolic blood pressure, rate of oxygen consumption (metabolic rate) and core body temperature.

FIG. 3 shows a 10:1:1 ratio of 8-SPT:CHA:Atropine is more effective at lowering oxygen consumption during exposure to a 4° C. cold surface than 15:1:1 and 25:1:1 ratios. Rats were pretreated with Atropine 1 mg/kg and either SPT 10 mg/kg, 15 mg/kg, or 25 mg/kg 15 minutes before CHA 1 mg/kg bolus was given and maintained at 0.25 mg/(kg h) IV. Rats were placed on a 4° C. cooled surface immediately after CHA bolus (n=5).

FIG. 4 shows a 10:1:1 8-SPT:CHA:Atropine prevents hypotension, but does not attenuate metabolic suppression shown in FIG. 1. Pretreatment with 8-SPT and Atropine prevents CHA induced hypotension. All doses of 8-SPT effectively blocked hypotension caused by CHA alone. Rats were pretreated with Atropine 1 mg/kg and either SPT 10 mg/kg, 15 mg/kg, or 25 mg/kg 15 minutes before CHA 1 mg/kg bolus was given and maintained at 0.25 mg/(kg·h) IV. Rats were placed on a 4° C. cooled surface immediately after CHA bolus (n=5).

FIG. 5 shows 8-SPT and atropine synergize to prevent CHA induced hypotension during induction of metabolic suppression. Here we show that pretreatment with Atropine or 8-SPT alone is not sufficient, but combined administration of 8-SPT and atropine prevent hypotension. Rats were pretreated 15 min before CHA 1 mg/kg administration with either Atropine 1 mg/kg (A51C), 8-SPT 25 m/kg (S15C), 1 mg/kg Atropine and 25 mg/kg 8-SPT (AS15C), or no pretreatment (C). Core body temperature, mean arterial pressure, heart rate, and oxygen consumption were measured. The break in oxygen consumption data was due to washout of the metabolic chamber after the lid was opened to place the animal in the chamber. Time of pretreatment administration is indicated by arrowhead (n=3-5).

FIG. 6 shows low or high dose of atropine alone does not prevent CHA-induced hypotension. Pretreatment with Atropine (1 mg/kg or 0.5 mg/kg) does not prevent CHA induced hypotension. Rats were pretreated 15 min before CHA 1 mg/kg administration with either Atropine 1 mg/kg (A15C), Atropine 1 mg/kg Atropine 0.5 mg/kg (T15C) or no pretreatment (C). Time of pretreatment administration is indicated by arrowhead. Core body temperature, mean arterial pressure, heart rate, and oxygen consumption were measured (n=3-5).

FIG. 7 shows after metabolic suppression is stabilized, 8-SPT alone is sufficient to increase blood pressure. Timing of 8-SPT administration relative to CHA result in different hemodynamic outcomes. Pretreatment of 8-SPT 25 mg/kg 15 min before CHA (S15C) had minimal effect on mean arterial pressure and heart rate compared to CHA 1 mg/kg alone (C). 8-SPT 25 mg/kg administered 30 min after CHA 1 mg/kg (C305) increased significantly heart rate, mean arterial pressure, oxygen consumption, and core body temperature. Time of pretreatment administration is indicated by arrowhead. (n=4-5).

FIG. 8 shows pretreatment with diphenhydramine and 8-SPT before CHA administration partially restores mean arterial pressure. Pretreatment with diphenhydramine or 8-SPT alone is not sufficient to prevent hypotension. Rats were administered either diphenhydramine 4 mg/kg, 30 min before CHA 1 mg/kg (D30C), 8-SPT 25 mg/kg, 15 min before CHA 1 mg/kg (S15C), diphenhydramine 4 mg/kg and 8-SPT 25 m/kg 15 min before CHA 1 mg/kg (DS15C), or no pretreatment (C). Time of pretreatment administration is indicated by arrowhead. Core body temperature, mean arterial pressure, heart rate, and oxygen consumption were measured (n=3-5).

FIG. 9 shows pretreatment with propranolol with 8-SPT weakly prevents the fall in mean arterial pressure. Pretreatment with propranolol or 8-SPT alone is not sufficient to prevent hypotension. Rats were pretreated 15 min before CHA 1 mg/kg administration with either propranolol 4 mg/kg (P15C), 8-SPT 25 m/kg (S15C), 4 mg/kg propranolol and 25 mg/kg 8-SPT (PS15C), or no pretreatment (C). Time of pretreatment administration is indicated by arrowhead. Core body temperature, mean arterial pressure, heart rate, and oxygen consumption were measured (n=3-5).

FIG. 10 shows combined administration of CHA with 8-SPT or CPA with 8-SPT does not prevent hypotension mediated by CHA or by CPA. The following drugs were administered at time point zero:CHA 1 mg/kg (C), CPA 1 mg/kg (P), a mixture of CHA 1 mg/kg with 8-SPT 10 mg/kg, and a mixture of CPA 1 mg/kg with 8-SPT 10 mg/kg. Core body temperature, mean arterial pressure, heart rate, and oxygen consumption were measured (n=4-5).

Figure 13:
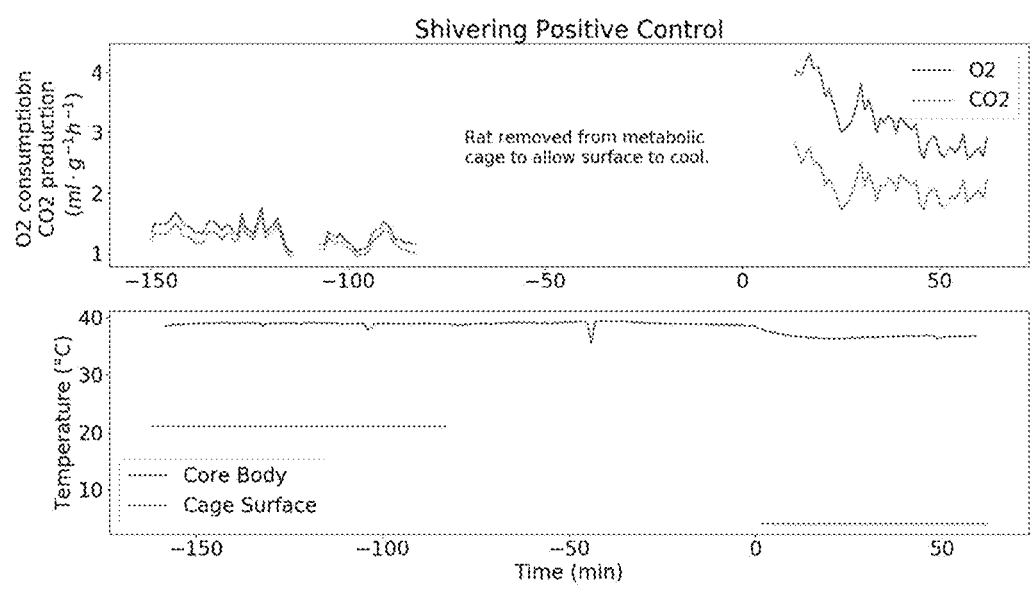

FIG. 13 shows shivering in response to cold exposure increases metabolic rate. This example represents a positive shivering control. To obtain baseline data a rat was placed in a metabolic chamber on a 20° C. maintained surface while oxygen consumption, carbon dioxide production and core body temperature were monitored. The averaged baseline values before cold exposure were: core body temperature 38.9° C., oxygen consumption 1.4 ml·g$^{-1}$ h$^{-1}$, and carbon dioxide production was 1.2 ml·g$^{-1}$ h$^{-1}$. After baseline values were obtained the rat was removed from the metabolic chamber to allow the surface to cool to 4° C. At time zero the rat was placed back into the metabolic chamber onto the 4° C. cooled surface after being sprayed lightly with 95% ethanol to facilitate evaporative cooling. The rat's core body temperature began to drop as immediately upon cold exposure. Core body temperature decreased 2.4° C., oxygen consumption increased to 3.25 ml·g$^{-1}$ h$^{-1}$, and carbon dioxide production increased 2.2 4 ml·g$^{-1}$ h$^{-1}$.

DETAILED DESCRIPTION

The following numbered clause embodiments are contemplated and are non-limiting:
1. A pharmaceutical composition comprising i) an A1 adenosine receptor (A1AR) agonist, ii) an A1AR antagonist, and iii) an anticholinergic.
2. A pharmaceutical composition consisting essentially of i) an A1 adenosine receptor (A1AR) agonist, ii) an A1AR antagonist, and iii) an anticholinergic.
3. A pharmaceutical composition consisting of i) an A1 adenosine receptor (A1AR) agonist, ii) an A1AR antagonist, and iii) an anticholinergic.
4. The pharmaceutical composition of any of clauses 1-3, any other suitable clause, or any combination of suitable clauses, wherein the A1AR agonist is a selective Adenosine A1 receptor agonist.
5. The pharmaceutical composition of any of clauses 1-3, any other suitable clause, or any combination of suitable clauses, wherein the A1AR agonist is a nonselective Adenosine A1 receptor agonist.
6. The pharmaceutical composition of any of clauses 1-3, any other suitable clause, or any combination of suitable clauses, wherein the A1AR antagonist is a selective Adenosine A1 receptor antagonist.
7. The pharmaceutical composition of any of clauses 1-3, any other suitable clause, or any combination of suitable clauses, wherein the A1AR antagonist is a nonselective Adenosine A1 receptor antagonist.
8. The pharmaceutical composition of any of clauses 1-3, any other suitable clause, or any combination of suitable clauses, wherein the A1AR antagonist is a peripherally acting Adenosine A1 receptor antagonist.
9. The pharmaceutical composition of any of clauses 1-3, any other suitable clause, or any combination of suitable clauses, wherein the A1AR antagonist has a CLogBB of about −2.0.
10. The pharmaceutical composition of any of clauses 1-3, any other suitable clause, or any combination of suitable clauses, wherein the A1AR antagonist has a CLogBB of less than about −2.0.
11. The pharmaceutical composition of any of clauses 1-3, any other suitable clause, or any combination of suitable clauses, wherein the A1AR antagonist has a CLogBB of less than or equal to about −2.0.
12. The pharmaceutical composition of any of clauses 1-3, any other suitable clause, or any combination of suitable clauses, wherein the anticholinergic is a muscarinic receptor antagonist.
13. The pharmaceutical composition of any of clauses 1-3, any other suitable clause, or any combination of suitable clauses, wherein the A1AR agonist comprises $^6$N-cyclohexyladenosine (CHA).
14. The pharmaceutical composition of clause 13, any other suitable clause, or any combination of suitable clauses, wherein the dose of CHA is present in a range between about 0.001 to about 1000 mg.
15. The pharmaceutical composition of any of clauses 1-3, any other suitable clause, or any combination of suitable clauses, wherein the A1AR antagonist comprises 8-(p-sulfophenyl) theophylline (8-SPT).
16. The pharmaceutical composition of clause 15, any other suitable clause, or any combination of suitable clauses, wherein the dose of 8-SPT is present in a range between about 0.001 to about 1000 mg.
17. The pharmaceutical composition of any of clauses 1-3, any other suitable clause, or any combination of suitable clauses, wherein the A1AR antagonist comprises a substituted theophylline, wherein the substituted theophylline is substituted at C7 with a cyclo group or an aryl group.
18. The pharmaceutical composition of clause 17, any other suitable clause, or any combination of suitable clauses, wherein the A1AR antagonist comprises a substituted theophylline, wherein the substituted theophylline is substituted at C7 with a group that is ionized at a pH between about 7 to about 7.5.
19. The pharmaceutical composition of any of clauses 1-3, any other suitable clause, or any combination of suitable clauses, wherein the anticholinergic comprises atropine, glycopyrrolate, or a combination thereof.
20. The pharmaceutical composition of any of clauses 1-3, any other suitable clause, or any combination of suitable clauses, wherein the anticholinergic is atropine.
21. The pharmaceutical composition of clause 20, any other suitable clause, or any combination of suitable clauses, wherein the dose of atropine is present in a range between about 0.001 to about 1000 mg.
22. The pharmaceutical composition of any of clauses 1-3, any other suitable clause, or any combination of suitable clauses, wherein the anticholinergic is glycopyrrolate.
23. The pharmaceutical composition of clause 22, any other suitable clause, or any combination of suitable clauses, wherein the dose of glycopyrrolate is present in a range between about 0.001 to about 1000 mg.
24. The pharmaceutical composition of any of clauses 1-3, any other suitable clause, or any combination of suitable clauses, wherein the pharmaceutical composition comprises a ratio of the A1AR agonist and the A1AR antagonist (mg/kg:mg/kg).
25. The pharmaceutical composition of clause 24, any other suitable clause, or any combination of suitable clauses, wherein the ratio is 25:1.
26. The pharmaceutical composition of clause 24, any other suitable clause, or any combination of suitable clauses, wherein the ratio is 24:1.
27. The pharmaceutical composition of clause 24, any other suitable clause, or any combination of suitable clauses, wherein the ratio is 23:1.
28. The pharmaceutical composition of clause 24, any other suitable clause, or any combination of suitable clauses, wherein the ratio is 22:1.
29. The pharmaceutical composition of clause 24, any other suitable clause, or any combination of suitable clauses, wherein the ratio is 21:1.
30. The pharmaceutical composition of clause 24, any other suitable clause, or any combination of suitable clauses, wherein the ratio is 20:1.
31. The pharmaceutical composition of clause 24, any other suitable clause, or any combination of suitable clauses, wherein the ratio is 19:1.
32. The pharmaceutical composition of clause 24, any other suitable clause, or any combination of suitable clauses, wherein the ratio is 18:1.
33. The pharmaceutical composition of clause 24, any other suitable clause, or any combination of suitable clauses, wherein the ratio is 17:1.
34. The pharmaceutical composition of clause 24, any other suitable clause, or any combination of suitable clauses, wherein the ratio is 16:1.

35. The pharmaceutical composition of clause 24, any other suitable clause, or any combination of suitable clauses, wherein the ratio is 15:1.
36. The pharmaceutical composition of clause 24, any other suitable clause, or any combination of suitable clauses, wherein the ratio is 14:1.
37. The pharmaceutical composition of clause 24, any other suitable clause, or any combination of suitable clauses, wherein the ratio is 13:1.
38. The pharmaceutical composition of clause 24, any other suitable clause, or any combination of suitable clauses, wherein the ratio is 12:1.
39. The pharmaceutical composition of clause 24, any other suitable clause, or any combination of suitable clauses, wherein the ratio is 11:1.
40. The pharmaceutical composition of clause 24, any other suitable clause, or any combination of suitable clauses, wherein the ratio is 10:1.
41. The pharmaceutical composition of clause 24, any other suitable clause, or any combination of suitable clauses, wherein the ratio is 9:1.
42. The pharmaceutical composition of clause 24, any other suitable clause, or any combination of suitable clauses, wherein the ratio is 8:1.
43. The pharmaceutical composition of clause 24, any other suitable clause, or any combination of suitable clauses, wherein the ratio is 7:1.
44. The pharmaceutical composition of clause 24, any other suitable clause, or any combination of suitable clauses, wherein the ratio is 6:1.
45. The pharmaceutical composition of clause 24, any other suitable clause, or any combination of suitable clauses, wherein the ratio is 5:1.
46. The pharmaceutical composition of clause 24, any other suitable clause, or any combination of suitable clauses, wherein the ratio is 4:1.
47. The pharmaceutical composition of clause 24, any other suitable clause, or any combination of suitable clauses, wherein the ratio is 3:1.
48. The pharmaceutical composition of clause 24, any other suitable clause, or any combination of suitable clauses, wherein the ratio is 2:1.
49. The pharmaceutical composition of clause 24, any other suitable clause, or any combination of suitable clauses, wherein the ratio is 1:1.
50. The pharmaceutical composition of clause 24, any other suitable clause, or any combination of suitable clauses, wherein the ratio is 0.5:1.
51. The pharmaceutical composition of clause 24, any other suitable clause, or any combination of suitable clauses, wherein the ratio is 0.25:1.
52. The pharmaceutical composition of any of clauses 1-3, any other suitable clause, or any combination of suitable clauses, wherein the pharmaceutical composition comprises a ratio of the A1AR agonist, the A1AR antagonist, and the anticholinergic (mg/kg:mg/kg:mg/kg).
53. The pharmaceutical composition of clause 52, any other suitable clause, or any combination of suitable clauses, wherein the ratio is 25:1:1.
54. The pharmaceutical composition of clause 52, any other suitable clause, or any combination of suitable clauses, wherein the ratio is 24:1:1.
55. The pharmaceutical composition of clause 52, any other suitable clause, or any combination of suitable clauses, wherein the ratio is 23:1:1.
56. The pharmaceutical composition of clause 52, any other suitable clause, or any combination of suitable clauses, wherein the ratio is 22:1:1.
57. The pharmaceutical composition of clause 52, any other suitable clause, or any combination of suitable clauses, wherein the ratio is 21:1:1.
58. The pharmaceutical composition of clause 52, any other suitable clause, or any combination of suitable clauses, wherein the ratio is 20:1:1.
59. The pharmaceutical composition of clause 52, any other suitable clause, or any combination of suitable clauses, wherein the ratio is 19:1:1.
60. The pharmaceutical composition of clause 52, any other suitable clause, or any combination of suitable clauses, wherein the ratio is 18:1:1.
61. The pharmaceutical composition of clause 52, any other suitable clause, or any combination of suitable clauses, wherein the ratio is 17:1:1.
62. The pharmaceutical composition of clause 52, any other suitable clause, or any combination of suitable clauses, wherein the ratio is 16:1:1.
63. The pharmaceutical composition of clause 52, any other suitable clause, or any combination of suitable clauses, wherein the ratio is 15:1:1.
64. The pharmaceutical composition of clause 52, any other suitable clause, or any combination of suitable clauses, wherein the ratio is 14:1:1.
65. The pharmaceutical composition of clause 52, any other suitable clause, or any combination of suitable clauses, wherein the ratio is 13:1:1.
66. The pharmaceutical composition of clause 52, any other suitable clause, or any combination of suitable clauses, wherein the ratio is 12:1:1.
67. The pharmaceutical composition of clause 52, any other suitable clause, or any combination of suitable clauses, wherein the ratio is 11:1:1.
68. The pharmaceutical composition of clause 52, any other suitable clause, or any combination of suitable clauses, wherein the ratio is 10:1:1.
69. The pharmaceutical composition of clause 52, any other suitable clause, or any combination of suitable clauses, wherein the ratio is 9:1:1.
70. The pharmaceutical composition of clause 52, any other suitable clause, or any combination of suitable clauses, wherein the ratio is 8:1:1.
71. The pharmaceutical composition of clause 52, any other suitable clause, or any combination of suitable clauses, wherein the ratio is 7:1:1.
72. The pharmaceutical composition of clause 52, any other suitable clause, or any combination of suitable clauses, wherein the ratio is 6:1:1.
73. The pharmaceutical composition of clause 52, any other suitable clause, or any combination of suitable clauses, wherein the ratio is 5:1:1.
74. The pharmaceutical composition of clause 52, any other suitable clause, or any combination of suitable clauses, wherein the ratio is 4:1:1.
75. The pharmaceutical composition of clause 52, any other suitable clause, or any combination of suitable clauses, wherein the ratio is 3:1:1.
76. The pharmaceutical composition of clause 52, any other suitable clause, or any combination of suitable clauses, wherein the ratio is 2:1:1.
77. The pharmaceutical composition of clause 52, any other suitable clause, or any combination of suitable clauses, wherein the ratio is 1:1:1.

78. The pharmaceutical composition of clause 52, any other suitable clause, or any combination of suitable clauses, wherein the ratio is 0.5:1:1.
79. The pharmaceutical composition of clause 52, any other suitable clause, or any combination of suitable clauses, wherein the ratio is 0.5:1:0.5.
80. The pharmaceutical composition of clause 52, any other suitable clause, or any combination of suitable clauses, wherein the ratio is 0.5:1:0.025.
81. The pharmaceutical composition of clause 52, any other suitable clause, or any combination of suitable clauses, wherein the ratio is 0.5:1:0.0125.
82. The pharmaceutical composition of clause 52, any other suitable clause, or any combination of suitable clauses, wherein the ratio is 40:4:1.
83. The pharmaceutical composition of clause 52, any other suitable clause, or any combination of suitable clauses, wherein the ratio is 39:4:1.
84. The pharmaceutical composition of clause 52, any other suitable clause, or any combination of suitable clauses, wherein the ratio is 38:4:1.
85. The pharmaceutical composition of clause 52, any other suitable clause, or any combination of suitable clauses, wherein the ratio is 37:4:1.
86. The pharmaceutical composition of clause 52, any other suitable clause, or any combination of suitable clauses, wherein the ratio is 36:4:1.
87. The pharmaceutical composition of clause 52, any other suitable clause, or any combination of suitable clauses, wherein the ratio is 35:4:1.
88. The pharmaceutical composition of clause 52, any other suitable clause, or any combination of suitable clauses, wherein the ratio is 34:4:1.
89. The pharmaceutical composition of clause 52, any other suitable clause, or any combination of suitable clauses, wherein the ratio is 33:4:1.
90. The pharmaceutical composition of clause 52, any other suitable clause, or any combination of suitable clauses, wherein the ratio is 32:4:1.
91. The pharmaceutical composition of clause 52, any other suitable clause, or any combination of suitable clauses, wherein the ratio is 31:4:1.
92. The pharmaceutical composition of clause 52, any other suitable clause, or any combination of suitable clauses, wherein the ratio is 30:4:1.
93. The pharmaceutical composition of clause 52, any other suitable clause, or any combination of suitable clauses, wherein the ratio is 29:4:1.
94. The pharmaceutical composition of clause 52, any other suitable clause, or any combination of suitable clauses, wherein the ratio is 28:4:1.
95. The pharmaceutical composition of clause 52, any other suitable clause, or any combination of suitable clauses, wherein the ratio is 27:4:1.
96. The pharmaceutical composition of clause 52, any other suitable clause, or any combination of suitable clauses, wherein the ratio is 26:4:1.
97. The pharmaceutical composition of clause 52, any other suitable clause, or any combination of suitable clauses, wherein the ratio is 25:4:1.
98. The pharmaceutical composition of clause 52, any other suitable clause, or any combination of suitable clauses, wherein the ratio is 24:4:1.
99. The pharmaceutical composition of clause 52, any other suitable clause, or any combination of suitable clauses, wherein the ratio is 23:4:1.
100. The pharmaceutical composition of clause 52, any other suitable clause, or any combination of suitable clauses, wherein the ratio is 22:4:1.
101. The pharmaceutical composition of clause 52, any other suitable clause, or any combination of suitable clauses, wherein the ratio is 21:4:1.
102. The pharmaceutical composition of clause 52, any other suitable clause, or any combination of suitable clauses, wherein the ratio is 20:4:1.
103. The pharmaceutical composition of clause 52, any other suitable clause, or any combination of suitable clauses, wherein the ratio is 19:4:1.
104. The pharmaceutical composition of clause 52, any other suitable clause, or any combination of suitable clauses, wherein the ratio is 18:4:1.
105. The pharmaceutical composition of clause 52, any other suitable clause, or any combination of suitable clauses, wherein the ratio is 17:4:1.
106. The pharmaceutical composition of clause 52, any other suitable clause, or any combination of suitable clauses, wherein the ratio is 16:4:1.
107. The pharmaceutical composition of clause 52, any other suitable clause, or any combination of suitable clauses, wherein the ratio is 15:4:1.
108. The pharmaceutical composition of clause 52, any other suitable clause, or any combination of suitable clauses, wherein the ratio is 14:4:1.
109. The pharmaceutical composition of clause 52, any other suitable clause, or any combination of suitable clauses, wherein the ratio is 13:4:1.
110. The pharmaceutical composition of clause 52, any other suitable clause, or any combination of suitable clauses, wherein the ratio is 12:4:1.
111. The pharmaceutical composition of clause 52, any other suitable clause, or any combination of suitable clauses, wherein the ratio is 11:4:1.
112. The pharmaceutical composition of clause 52, any other suitable clause, or any combination of suitable clauses, wherein the ratio is 10:4:1.
113. The pharmaceutical composition of clause 52, any other suitable clause, or any combination of suitable clauses, wherein the ratio is 9:4:1.
114. The pharmaceutical composition of clause 52, any other suitable clause, or any combination of suitable clauses, wherein the ratio is 8:4:1.
115. The pharmaceutical composition of clause 52, any other suitable clause, or any combination of suitable clauses, wherein the ratio is 7:4:1.
116. The pharmaceutical composition of clause 52, any other suitable clause, or any combination of suitable clauses, wherein the ratio is 6:4:1.
117. The pharmaceutical composition of clause 52, any other suitable clause, or any combination of suitable clauses, wherein the ratio is 5:4:1.
118. The pharmaceutical composition of clause 52, any other suitable clause, or any combination of suitable clauses, wherein the ratio is 4:4:1.
119. The pharmaceutical composition of clause 52, any other suitable clause, or any combination of suitable clauses, wherein the ratio is 40:2:1.
120. The pharmaceutical composition of clause 52, any other suitable clause, or any combination of suitable clauses, wherein the ratio is 39:2:1.
121. The pharmaceutical composition of clause 52, any other suitable clause, or any combination of suitable clauses, wherein the ratio is 38:2:1.

122. The pharmaceutical composition of clause 52, any other suitable clause, or any combination of suitable clauses, wherein the ratio is 37:2:1.
123. The pharmaceutical composition of clause 52, any other suitable clause, or any combination of suitable clauses, wherein the ratio is 36:2:1.
124. The pharmaceutical composition of clause 52, any other suitable clause, or any combination of suitable clauses, wherein the ratio is 35:2:1.
125. The pharmaceutical composition of clause 52, any other suitable clause, or any combination of suitable clauses, wherein the ratio is 34:2:1.
126. The pharmaceutical composition of clause 52, any other suitable clause, or any combination of suitable clauses, wherein the ratio is 33:2:1.
127. The pharmaceutical composition of clause 52, any other suitable clause, or any combination of suitable clauses, wherein the ratio is 32:2:1.
128. The pharmaceutical composition of clause 52, any other suitable clause, or any combination of suitable clauses, wherein the ratio is 31:2:1.
129. The pharmaceutical composition of clause 52, any other suitable clause, or any combination of suitable clauses, wherein the ratio is 30:2:1.
130. The pharmaceutical composition of clause 52, any other suitable clause, or any combination of suitable clauses, wherein the ratio is 29:2:1.
131. The pharmaceutical composition of clause 52, any other suitable clause, or any combination of suitable clauses, wherein the ratio is 28:2:1.
132. The pharmaceutical composition of clause 52, any other suitable clause, or any combination of suitable clauses, wherein the ratio is 27:2:1.
133. The pharmaceutical composition of clause 52, any other suitable clause, or any combination of suitable clauses, wherein the ratio is 26:2:1.
134. The pharmaceutical composition of clause 52, any other suitable clause, or any combination of suitable clauses, wherein the ratio is 25:2:1.
135. The pharmaceutical composition of clause 52, any other suitable clause, or any combination of suitable clauses, wherein the ratio is 24:2:1.
136. The pharmaceutical composition of clause 52, any other suitable clause, or any combination of suitable clauses, wherein the ratio is 23:2:1.
137. The pharmaceutical composition of clause 52, any other suitable clause, or any combination of suitable clauses, wherein the ratio is 22:2:1.
138. The pharmaceutical composition of clause 52, any other suitable clause, or any combination of suitable clauses, wherein the ratio is 21:2:1.
139. The pharmaceutical composition of clause 52, any other suitable clause, or any combination of suitable clauses, wherein the ratio is 20:2:1.
140. The pharmaceutical composition of clause 52, any other suitable clause, or any combination of suitable clauses, wherein the ratio is 19:2:1.
141. The pharmaceutical composition of clause 52, any other suitable clause, or any combination of suitable clauses, wherein the ratio is 18:2:1.
142. The pharmaceutical composition of clause 52, any other suitable clause, or any combination of suitable clauses, wherein the ratio is 17:2:1.
143. The pharmaceutical composition of clause 52, any other suitable clause, or any combination of suitable clauses, wherein the ratio is 16:2:1.
144. The pharmaceutical composition of clause 52, any other suitable clause, or any combination of suitable clauses, wherein the ratio is 15:2:1.
145. The pharmaceutical composition of clause 52, any other suitable clause, or any combination of suitable clauses, wherein the ratio is 14:2:1.
146. The pharmaceutical composition of clause 52, any other suitable clause, or any combination of suitable clauses, wherein the ratio is 13:2:1.
147. The pharmaceutical composition of clause 52, any other suitable clause, or any combination of suitable clauses, wherein the ratio is 12:2:1.
148. The pharmaceutical composition of clause 52, any other suitable clause, or any combination of suitable clauses, wherein the ratio is 11:2:1.
149. The pharmaceutical composition of clause 52, any other suitable clause, or any combination of suitable clauses, wherein the ratio is 10:2:1.
150. The pharmaceutical composition of any of clauses 1-3, any other suitable clause, or any combination of suitable clauses, wherein the pharmaceutical composition is a parenteral formulation.
151. The pharmaceutical composition of clause 150, any other suitable clause, or any combination of suitable clauses, wherein the parenteral formulation is an intravenous parenteral formulation.
152. The pharmaceutical composition of clause 150, any other suitable clause, or any combination of suitable clauses, wherein the parenteral formulation is a subcutaneous parenteral formulation.
153. The pharmaceutical composition of clause 150, any other suitable clause, or any combination of suitable clauses, wherein the parenteral formulation is an intramuscular parenteral formulation.
154. The pharmaceutical composition of any of clauses 1-3, any other suitable clause, or any combination of suitable clauses, wherein the pharmaceutical composition is an oral formulation.
155. The pharmaceutical composition of any of clauses 1-3, any other suitable clause, or any combination of suitable clauses, wherein the pharmaceutical composition is an intranasal formulation.
156. The pharmaceutical composition of any of clauses 1-3, any other suitable clause, or any combination of suitable clauses, wherein the pharmaceutical composition comprises a pharmaceutically acceptable carrier.
157. The pharmaceutical composition of clause 156, any other suitable clause, or any combination of suitable clauses, wherein the pharmaceutically acceptable carrier is selected from the group consisting of selected from the group consisting of saline, glucose, alcohols, glycols, esters, amides, and a combination thereof.
158. The pharmaceutical composition of any of clauses 1-3, any other suitable clause, or any combination of suitable clauses, wherein the pharmaceutical composition comprises a further active pharmaceutical ingredient (API).
159. The pharmaceutical composition of any of clauses 1-3, any other suitable clause, or any combination of suitable clauses, wherein the pharmaceutical composition is a unit dose.
160. The pharmaceutical composition of any of clauses 1-3, any other suitable clause, or any combination of suitable clauses, wherein the pharmaceutical composition is a single unit dose.
161. The pharmaceutical composition of any of clauses 1-3, any other suitable clause, or any combination of suitable 161. (continued) clauses, wherein the pharmaceutical composition provides synergistic suppression of metabolism.
162. The pharmaceutical composition of any of clauses 1-3, any other suitable clause, or any combination of suitable clauses, wherein the pharmaceutical composition provides synergistic suppression of metabolism.
163. The pharmaceutical composition of clause 162, any other suitable clause, or any combination of suitable clauses, wherein the suppression of metabolism is present without concomitant hypotension.
164. The pharmaceutical composition of any of clauses 1-3, any other suitable clause, or any combination of suitable clauses, wherein the pharmaceutical composition provides mitigation of a CHA-induced effect.
165. The pharmaceutical composition of clause 164, any other suitable clause, or any combination of suitable clauses, wherein the pharmaceutical composition provides synergistic mitigation of the CHA-induced effect.
166. The pharmaceutical composition of clause 164, any other suitable clause, or any combination of suitable clauses, wherein the mitigation is present during induction of metabolic suppression.
167. The pharmaceutical composition of clause 164, any other suitable clause, or any combination of suitable clauses, wherein the CHA-induced effect is selected from the group consisting of hypotension, centrally-mediated hypotension, peripherally-mediated hypotension, bradycardia, metabolic suppression, hypothermia, decreased rate of oxygen consumption (metabolic rate), and decreased mean arterial pressure (MAP).
168. The pharmaceutical composition of clause 164, any other suitable clause, or any combination of suitable clauses, wherein the CHA-induced effect is hypotension.
169. The pharmaceutical composition of clause 164, any other suitable clause, or any combination of suitable clauses, wherein the CHA-induced effect is centrally-mediated hypotension.
170. The pharmaceutical composition of clause 164, any other suitable clause, or any combination of suitable clauses, wherein the CHA-induced effect is peripherally-mediated hypotension.
171. The pharmaceutical composition of clause 164, any other suitable clause, or any combination of suitable clauses, wherein the CHA-induced effect is bradycardia.
172. The pharmaceutical composition of clause 164, any other suitable clause, or any combination of suitable clauses, wherein the CHA-induced effect is metabolic suppression.
173. The pharmaceutical composition of clause 164, any other suitable clause, or any combination of suitable clauses, wherein the CHA-induced effect is hypothermia.
174. The pharmaceutical composition of clause 164, any other suitable clause, or any combination of suitable clauses, wherein the CHA-induced effect is decreased rate of oxygen consumption (metabolic rate).
175. The pharmaceutical composition of clause 164, any other suitable clause, or any combination of suitable clauses, wherein the CHA-induced effect is decreased mean arterial pressure (MAP).
176. A kit comprising i) an A1 adenosine receptor (A1AR) agonist, ii) an A1AR antagonist, iii) an anticholinergic, and iv) a pharmaceutically acceptable carrier.
177. A kit consisting essentially of i) an A1 adenosine receptor (A1AR) agonist, ii) an A1AR antagonist, iii) an anticholinergic, and iv) a pharmaceutically acceptable carrier.
178. A kit consisting of i) an A1 adenosine receptor (A1AR) agonist, ii) an A1AR antagonist, iii) an anticholinergic, and iv) a pharmaceutically acceptable carrier.
179. A method of inducing metabolic depression in a patient, said method comprising the step of administrating a pharmaceutical composition comprising i) an A1 adenosine receptor (A1AR) agonist, ii) an A1AR antagonist, and iii) an anticholinergic to the patient, wherein the administration induces metabolic depression in the patient.
180. The method of clause 179, any other suitable clause, or any combination of suitable clauses, wherein the method prevents hypotension in the patient.
181. The method of clause 180, any other suitable clause, or any combination of suitable clauses, wherein the hypotension is centrally-mediated hypotension.
182. The method of clause 180, any other suitable clause, or any combination of suitable clauses, wherein the hypotension is peripherally-mediated hypotension.
183. The method of clause 179, any other suitable clause, or any combination of suitable clauses, wherein the method prevents bradycardia in the patient.
184. The method of clause 179, any other suitable clause, or any combination of suitable clauses, wherein the method prevents hypotension in the patient and prevents bradycardia in the patient.
185. The method of clause 184, any other suitable clause, or any combination of suitable clauses, wherein the hypotension is centrally-mediated hypotension.
186. The method of clause 184, any other suitable clause, or any combination of suitable clauses, wherein the hypotension is peripherally-mediated hypotension.
187. The method of clause 179, any other suitable clause, or any combination of suitable clauses, wherein the method further comprises administration of a further active pharmaceutical ingredient (API) to the patient.
188. The method of clause 179, any other suitable clause, or any combination of suitable clauses, wherein the pharmaceutical composition is administered as a single dose.
189. The method of clause 179, any other suitable clause, or any combination of suitable clauses, wherein the pharmaceutical composition is administered as a single unit dose.
190. The method of any one of clauses 179 to 189, any other suitable clause, or any combination of suitable clauses, wherein the pharmaceutical composition comprises the pharmaceutical composition of any of clauses 1 to 175.
191. A method of preventing hypotension in a patient, said method comprising the step of administrating a pharmaceutical composition comprising i) an A1 adenosine receptor (A1AR) agonist, ii) an A1AR antagonist, and iii) an anticholinergic to the patient, wherein the administration prevents hypotension in the patient.
192. The method of clause 191, any other suitable clause, or any combination of suitable clauses, wherein the hypotension is centrally-mediated hypotension.
193. The method of clause 191, any other suitable clause, or any combination of suitable clauses, wherein the hypotension is peripherally-mediated hypotension.
194. The method of clause 191, any other suitable clause, or any combination of suitable clauses, wherein the method induces metabolic depression in the patient.
195. The method of clause 191, any other suitable clause, or any combination of suitable clauses, wherein the method prevents bradycardia in the patient.

196. The method of clause 191, any other suitable clause, or any combination of suitable clauses, wherein the method induces metabolic depression in the patient and prevents bradycardia in the patient.

197. The method of clause 191, any other suitable clause, or any combination of suitable clauses, wherein the method further comprises administration of a further active pharmaceutical ingredient (API) to the patient.

198. The method of any one of clauses 191 to 197, any other suitable clause, or any combination of suitable clauses, wherein the pharmaceutical composition comprises the pharmaceutical composition of any of clauses 1 to 175.

199. A method of preventing bradycardia in a patient, said method comprising the step of administrating a pharmaceutical composition comprising i) an A1 adenosine receptor (A1AR) agonist, ii) an A1AR antagonist, and iii) an anticholinergic to the patient, wherein the administration prevents bradycardia in the patient.

200. The method of clause 199, any other suitable clause, or any combination of suitable clauses, wherein the method induces metabolic depression in the patient.

201. The method of clause 199, any other suitable clause, or any combination of suitable clauses, wherein the method prevents hypotension in the patient.

202. The method of clause 201, any other suitable clause, or any combination of suitable clauses, wherein the hypotension is centrally-mediated hypotension.

203. The method of clause 201, any other suitable clause, or any combination of suitable clauses, wherein the hypotension is peripherally-mediated hypotension.

204. The method of clause 199, any other suitable clause, or any combination of suitable clauses, wherein the method induces metabolic depression in the patient and prevents hypotension in the patient.

205. The method of clause 204, any other suitable clause, or any combination of suitable clauses, wherein the hypotension is centrally-mediated hypotension.

206. The method of clause 204, any other suitable clause, or any combination of suitable clauses, wherein the hypotension is peripherally-mediated hypotension.

207. The method of clause 199, any other suitable clause, or any combination of suitable clauses, wherein the method further comprises administration of a further active pharmaceutical ingredient (API) to the patient.

208. The method of any one of clauses 199 to 207, any other suitable clause, or any combination of suitable clauses, wherein the pharmaceutical composition comprises the pharmaceutical composition of any of clauses 1 to 175.

209. The kit of any one of clauses 176 to 178, any other suitable clause, or any combination of suitable clauses, wherein the kit comprises one or more elements of the pharmaceutical composition of any one of clauses 1 to 175.

In an aspect, a pharmaceutical composition is provided. The pharmaceutical composition comprises i) an A1 adenosine receptor (A1AR) agonist, ii) an A1 AR antagonist, and iii) an anticholinergic. Alternatively, the pharmaceutical composition consists essentially of i) an A1AR agonist, ii) an A1AR antagonist, and iii) an anticholinergic. Alternatively, the pharmaceutical composition consists of i) an A1AR agonist, ii) an A1AR antagonist, and iii) an anticholinergic.

In an aspect, a kit is provided. The kit comprises i) an A1 adenosine receptor (A1AR) agonist, ii) an A1AR antagonist, iii) an anticholinergic, and iv) a pharmaceutically acceptable carrier. Alternatively, the kit consists essentially of i) an A1AR agonist, ii) an A1AR antagonist, iii) an anticholinergic, and iv) a pharmaceutically acceptable carrier. Alternatively, the kit consists of i) an A1AR agonist, ii) an A1AR antagonist, iii) an anticholinergic, and iv) a pharmaceutically acceptable carrier.

In an aspect, a method of inducing metabolic depression in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration induces metabolic depression in the patient.

In an aspect, a method of preventing hypotension in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration prevents hypotension in the patient.

In an aspect, a method of preventing bradycardia in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration prevents bradycardia in the patient.

In one aspect, a pharmaceutical composition is provided. The pharmaceutical composition comprises i) an A1 adenosine receptor (A1AR) agonist, ii) an A1 AR antagonist, and iii) an anticholinergic. Alternatively, the pharmaceutical composition consists essentially of i) an A1AR agonist, ii) an A1AR antagonist, and iii) an anticholinergic. Alternatively, the pharmaceutical composition consists of i) an A1AR agonist, ii) an A1AR antagonist, and iii) an anticholinergic.

In an embodiment, the A1AR agonist is a selective Adenosine A1 receptor agonist. In an embodiment, the A1AR agonist is a nonselective Adenosine A1 receptor agonist.

In an embodiment, the A1AR antagonist is a selective Adenosine A1 receptor antagonist. In an embodiment, the A1AR antagonist is a nonselective Adenosine A1 receptor antagonist. In an embodiment, the A1AR antagonist is a peripherally acting Adenosine A1 receptor antagonist.

In an embodiment, the A1AR antagonist has a CLogBB of about −2.0. The CLogBB can be calculated, for example, in IIab and can assist in evaluating peripheral vs CNS action of a particular pharmaceutical agent. In an embodiment, the A1AR antagonist has a CLogBB of less than about −2.0. In an embodiment, the A1AR antagonist has a CLogBB of less than or equal to about −2.0.

Additional pharmaceutical agents according to the present disclosure, including various agonists and antagonists, are included in U.S. Provisional Application Ser. No. 63/160,356, incorporated herein by reference in its entirety.

In an embodiment, the anticholinergic is a muscarinic receptor antagonist.

In an embodiment, the A1AR agonist comprises 6N-cyclohexyladenosine (CHA). The chemical structure of CHA is:

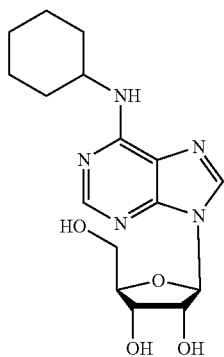

As used herein, the term "CHA" refers to CHA base, pharmaceutically acceptable salts of CHA, other salts of CHA, metabolites of CHA, and prodrugs of CHA. The term "pharmaceutically acceptable salt" refers to an addition salt that exists in conjunction with the acidic or basic portion of CHA. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when CHA and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when CHA and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In an embodiment, the dose of CHA is present in a range between about 0.001 to about 1000 mg.

In an embodiment, the A1AR antagonist comprises 8-(p-sulfophenyl) theophylline (8-SPT). The chemical structure of 8-SPT is:

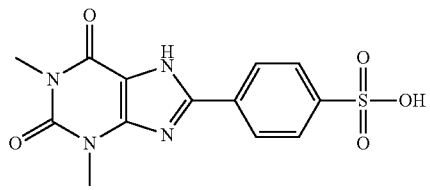 [SMILES: Cn1c(=O)c2[nH]c(-c3ccc(S(=O)(=O)O)cc3)nc2n(C)c1=O]

As used herein, the term "8-SPT" refers to 8-SPT base, pharmaceutically acceptable salts of 8-SPT, other salts of 8-SPT, metabolites of 8-SPT, and prodrugs of 8-SPT. The term "pharmaceutically acceptable salt" refers to an addition salt that exists in conjunction with the acidic or basic portion of 8-SPT. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when 8-SPT and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when 8-SPT and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In an embodiment, the dose of 8-SPT is present in a range between about 0.001 to about 1000 mg.

In an embodiment, the A1AR antagonist comprises a substituted theophylline, wherein the substituted theophylline is substituted at C7 with a cyclo group or an aryl group. In an embodiment, the A1AR antagonist comprises a substituted theophylline, wherein the substituted theophylline is substituted at C7 with a group that is ionized at a pH between about 7 to about 7.5.

In an embodiment, the anticholinergic comprises atropine, glycopyrrolate, or a combination thereof. In an embodiment, the anticholinergic is atropine. The chemical structure of atropine is:

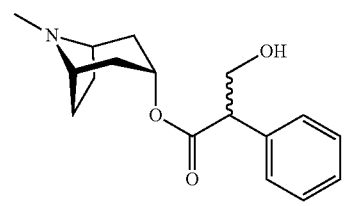

As used herein, the term "atropine" refers to atropine base, pharmaceutically acceptable salts of atropine, other salts of atropine, metabolites of atropine, and prodrugs of atropine. The term "pharmaceutically acceptable salt" refers to an addition salt that exists in conjunction with the acidic or basic portion of atropine. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when atropine and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when atropine and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In an embodiment, the dose of atropine is present in a range between about 0.001 to about 1000 mg.

In an embodiment, the anticholinergic is glycopyrrolate. The chemical structure of glycopyrrolate is:

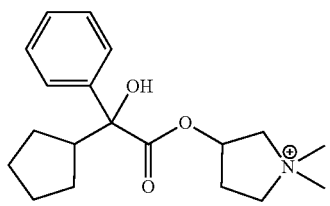 [SMILES: C[N+]1(C)CCC(OC(=O)C(O)(c2ccccc2)C2CCCC2)C1]

As used herein, the term "glycopyrrolate" refers to glycopyrrolate base, pharmaceutically acceptable salts of glycopyrrolate, other salts of glycopyrrolate, metabolites of glycopyrrolate, and prodrugs of glycopyrrolate. The term "pharmaceutically acceptable salt" refers to an addition salt that exists in conjunction with the acidic or basic portion of glycopyrrolate. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when glycopyrrolate and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when glycopyrrolate and any of its intermediates containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the present invention. They may serve as intermediates in the purification of compounds or in the preparation of other pharmaceutically-acceptable salts, or are useful for identification, characterization or purification.

In an embodiment, the dose of glycopyrrolate is present in a range between about 0.001 to about 1000 mg.

In an embodiment, the pharmaceutical composition comprises a ratio of the A1AR agonist and the A1AR antagonist (mg/kg:mg/kg). The ratio of the A1AR agonist and the A1AR antagonist is contemplated to vary depending on a particular stage of disease state of a patient. For instance, a patient may possess a stage of a disease state that requires a particular ratio and, upon a change of the stage, the patient may require a different ratio. In a specific example, a patient may require a first ratio in a disease state requiring an initial metabolic suppression, a second ratio in a disease state requiring maintenance of suppressed metabolism, and a third ratio in a disease state requiring return to normal metabolism. The various stages and their related ratios can be determined by a person of ordinary skill in the art according to the present disclosure. Additional ratios for the described embodiments are included in U.S. Provisional Application Ser. No. 63/160,356, incorporated herein by reference in its entirety.

In an embodiment, the ratio is 25:1. In an embodiment, the ratio is 24:1. In an embodiment, the ratio is 23:1. In an embodiment, the ratio is 22:1. In an embodiment, the ratio is 21:1. In an embodiment, the ratio is 20:1. In an embodiment, the ratio is 19:1. In an embodiment, the ratio is 18:1. In an embodiment, the ratio is 17:1. In an embodiment, the ratio is 16:1. In an embodiment, the ratio is 15:1. In an embodiment, the ratio is 14:1. In an embodiment, the ratio is 13:1. In an embodiment, the ratio is 12:1. In an embodiment, the ratio is 11:1. In an embodiment, the ratio is 10:1. In an embodiment, the ratio is 9:1. In an embodiment, the ratio is 8:1. In an embodiment, the ratio is 7:1. In an embodiment, the ratio is 6:1. In an embodiment, the ratio is 5:1. In an embodiment, the ratio is 4:1. In an embodiment, the ratio is 3:1. In an embodiment, the ratio is 2:1. In an embodiment, the ratio is 1:1. In an embodiment, the ratio is 0.5:1. In an embodiment, the ratio is 0.25:1.

In an embodiment, the pharmaceutical composition comprises a ratio of the A1AR agonist, the A1AR antagonist, and the anticholinergic (mg/kg:mg/kg:mg/kg). The ratio of the A1AR agonist, the A1AR antagonist, and the anticholinergic is contemplated to vary depending on a particular stage of disease state of a patient as described herein.

In an embodiment, the ratio is 25:1:1. In an embodiment, the ratio is 24:1:1. In an embodiment, the ratio is 23:1:1. In an embodiment, the ratio is 22:1:1. In an embodiment, the ratio is 21:1:1. In an embodiment, the ratio is 20:1:1. In an embodiment, the ratio is 19:1:1. In an embodiment, the ratio is 18:1:1. In an embodiment, the ratio is 17:1:1. In an embodiment, the ratio is 16:1:1. In an embodiment, the ratio is 15:1:1. In an embodiment, the ratio is 14:1:1. In an embodiment, the ratio is 13:1:1. In an embodiment, the ratio is 12:1:1. In an embodiment, the ratio is 11:1:1. In an embodiment, the ratio is 10:1:1. In an embodiment, the ratio is 9:1:1. In an embodiment, the ratio is 8:1:1. In an embodiment, the ratio is 7:1:1. In an embodiment, the ratio is 6:1:1. In an embodiment, the ratio is 5:1:1. In an embodiment, the ratio is 4:1:1. In an embodiment, the ratio is 3:1:1. In an embodiment, the ratio is 2:1:1. In an embodiment, the ratio is 1:1:1. In an embodiment, the ratio is 0.5:1:1. In an embodiment, the ratio is 0.5:1:0.5. In an embodiment, the ratio is 0.5:1:0.025. In an embodiment, the ratio is 0.5:1:0.0125. In an embodiment, the ratio is 40:4:1. In an embodiment, the ratio is 39:4:1. In an embodiment, the ratio is 38:4:1. In an embodiment, the ratio is 37:4:1. In an embodiment, the ratio is 36:4:1. In an embodiment, the ratio is 35:4:1. In an embodiment, the ratio is 34:4:1. In an embodiment, the ratio is 33:4:1. In an embodiment, the ratio is 32:4:1. In an embodiment, the ratio is 31:4:1. In an embodiment, the ratio is 30:4:1. In an embodiment, the ratio is 29:4:1. In an embodiment, the ratio is 28:4:1. In an embodiment, the ratio is 27:4:1. In an embodiment, the ratio is 26:4:1. In an embodiment, the ratio is 25:4:1. In an embodiment, the ratio is 24:4:1. In an embodiment, the ratio is 23:4:1. In an embodiment, the ratio is 22:4:1. In an embodiment, the ratio is 21:4:1. In an embodiment, the ratio is 20:4:1. In an embodiment, the ratio is 19:4:1. In an embodiment, the ratio is 18:4:1. In an embodiment, the ratio is 17:4:1. In an embodiment, the ratio is 16:4:1. In an embodiment, the ratio is 15:4:1. In an embodiment, the ratio is 14:4:1. In an embodiment, the ratio is 13:4:1. In an embodiment, the ratio is 12:4:1. In an embodiment, the ratio is 11:4:1. In an embodiment, the ratio is 10:4:1. In an embodiment, the ratio is 9:4:1. In an embodiment, the ratio is 8:4:1.

In an embodiment, the ratio is 7:4:1. In an embodiment, the ratio is 6:4:1. In an embodiment, the ratio is 5:4:1. In an embodiment, the ratio is 4:4:1. In an embodiment, the ratio is 40:2:1. In an embodiment, the ratio is 39:2:1. In an embodiment, the ratio is 38:2:1. In an embodiment, the ratio is 37:2:1. In an embodiment, the ratio is 36:2:1. In an embodiment, the ratio is 35:2:1. In an embodiment, the ratio is 34:2:1. In an embodiment, the ratio is 33:2:1. In an embodiment, the ratio is 32:2:1. In an embodiment, the ratio is 31:2:1. In an embodiment, the ratio is 30:2:1. In an embodiment, the ratio is 29:2:1. In an embodiment, the ratio is 28:2:1. In an embodiment, the ratio is 27:2:1. In an embodiment, the ratio is 26:2:1. In an embodiment, the ratio is 25:2:1. In an embodiment, the ratio is 24:2:1. In an embodiment, the ratio is 23:2:1. In an embodiment, the ratio is 22:2:1. In an embodiment, the ratio is 21:2:1. In an embodiment, the ratio is 20:2:1. In an embodiment, the ratio is 19:2:1. In an embodiment, the ratio is 18:2:1. In an embodiment, the ratio is 17:2:1. In an embodiment, the ratio is 16:2:1. In an embodiment, the ratio is 15:2:1. In an embodiment, the ratio is 14:2:1. In an embodiment, the ratio is 13:2:1. In an embodiment, the ratio is 12:2:1. In an embodiment, the ratio is 11:2:1. In an embodiment, the ratio is 10:2:1.

In an embodiment, the pharmaceutical composition is a parenteral formulation. The term "parenteral formulation" refers to a formulation suitable for the administration of the pharmaceutical composition via injection under or through one or more layers of skin or mucus membranes of an animal, such as a human. Standard parenteral injections are given into the intradermal, subcutaneous, or intramuscular region of an animal. In an embodiment, the parenteral formulation is an intravenous parenteral formulation. In an embodiment, the parenteral formulation is a subcutaneous parenteral formulation. In an embodiment, the parenteral formulation is an intramuscular parenteral formulation.

In an embodiment, the pharmaceutical composition is an oral formulation. The term "oral formulation" refers to the provision of the pharmaceutical composition via the mouth through ingestion, or via some other part of the gastrointestinal system including the esophagus. Examples of oral dosage forms include tablets (including compressed, coated or uncoated), capsules, hard or soft gelatin capsules, pellets, pills, powders, granules, elixirs, tinctures, colloidal dispersions, dispersions, effervescent compositions, films, sterile solutions or suspensions, syrups and emulsions and the like.

In an embodiment, the pharmaceutical composition is an intranasal formulation. The term "intranasal formulation" refers to the provision of the pharmaceutical composition occurring within or administered through the nose.

In an embodiment, the pharmaceutical composition comprises a pharmaceutically acceptable carrier. As used herein, the term "pharmaceutically acceptable carrier" refers to any agents which do not cause an intolerable side effect and which allow the active ingredients in the pharmaceutical composition to retain their pharmacological activities. A pharmaceutically acceptable carrier includes excipients, emulsifiers, solubilizers, surfactants, buffers, preservatives, and/or other additives which may enhance stability, delivery, absorption, half-life, efficacy, pharmacokinetics, pharmacodynamics, reduce adverse side effect or provide other advantages for pharmaceutical use. In an embodiment, the pharmaceutically acceptable carrier is selected from the group consisting of selected from the group consisting of saline, glucose, alcohols, glycols, esters, amides, and a combination thereof. In an embodiment, the pharmaceutical composition comprises a further active pharmaceutical ingredient (API).

In an embodiment, the pharmaceutical composition is a unit dose. In an embodiment, the pharmaceutical composition is a single unit dose. As used herein, the term "unit dose" is a discrete amount of the pharmaceutical composition comprising a predetermined amount of one or more components. The amount of the components is generally equal to the dosage of the components which would be administered to an animal or a convenient fraction of such a dosage such as, for example, one-half or one-third of such a dosage.

According to the methods of the present disclosure, the terms "single dose" and "single unit dose" include embodiments wherein the pharmaceutical composition can be administered as a single parenteral injection or administered as multiple parenteral injections. In one embodiment, a single dose or single unit dose of the composition can be parenterally administered to an animal at one location on the animal's body. In another embodiment, a single dose or single unit dose of the composition can be parenterally administered to an animal in multiple injections at a single location on the animal's body. In yet another embodiment, a single dose or single unit dose of the composition can be parenterally administered to an animal in multiple injections at more than one location on the animal's body. In embodiments wherein multiple injections of the composition are utilized, the multiple injections can be administered to the animal over a reasonable duration of time.

In an embodiment, the pharmaceutical composition provides synergistic suppression of metabolism. In an embodiment, the pharmaceutical composition provides synergistic suppression of metabolism. In an embodiment, the suppression of metabolism is present without concomitant hypotension.

In an embodiment, the pharmaceutical composition provides mitigation of a CHA-induced effect. In an embodiment, the pharmaceutical composition provides synergistic mitigation of the CHA-induced effect. In an embodiment, the mitigation is present during induction of metabolic suppression. In an embodiment, the CHA-induced effect is selected from the group consisting of hypotension, centrally-mediated hypotension, peripherally-mediated hypotension, bradycardia, metabolic suppression, hypothermia, decreased rate of oxygen consumption (metabolic rate), and decreased mean arterial pressure (MAP).

In an embodiment, the CHA-induced effect is hypotension. In an embodiment, the CHA-induced effect is centrally-mediated hypotension. In an embodiment, the CHA-induced effect is peripherally-mediated hypotension. In an embodiment, the CHA-induced effect is bradycardia. In an embodiment, the CHA-induced effect is metabolic suppression. In an embodiment, the CHA-induced effect is hypothermia. In an embodiment, the CHA-induced effect is decreased rate of oxygen consumption (metabolic rate). In an embodiment, the CHA-induced effect is decreased mean arterial pressure (MAP).

In one aspect, a kit is provided. The kit comprises i) an A1 adenosine receptor (A1AR) agonist, ii) an A1AR antagonist, iii) an anticholinergic, and iv) a pharmaceutically acceptable carrier. Alternatively, the kit consists essentially of i) an A1AR agonist, ii) an A1AR antagonist, iii) an anticholinergic, and iv) a pharmaceutically acceptable carrier. Alternatively, the kit consists of i) an A1AR agonist, ii) an A1AR antagonist, iii) an anticholinergic, and iv) a pharmaceutically acceptable carrier.

The previously described embodiments of the pharmaceutical composition are applicable to the kit described herein.

In one aspect, a method of inducing metabolic depression in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration induces metabolic depression in the patient.

The previously described embodiments of the pharmaceutical composition and the kit are applicable to the method of inducing metabolic depression in a patient described herein.

In an embodiment, the method prevents hypotension in the patient. In an embodiment, the hypotension is centrally-mediated hypotension. In an embodiment, the hypotension is peripherally-mediated hypotension. In an embodiment, the method prevents bradycardia in the patient. In an embodiment, the method prevents hypotension in the patient and prevents bradycardia in the patient. In an embodiment, the hypotension is centrally-mediated hypotension. In an embodiment, the hypotension is peripherally-mediated hypotension. In an embodiment, the method further comprises administration of a further active pharmaceutical ingredient (API) to the patient. In an embodiment, the pharmaceutical composition is administered as a single dose. In an embodiment, the pharmaceutical composition is administered as a single unit dose.

In one aspect, a method of preventing hypotension in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration prevents hypotension in the patient.

The previously described embodiments of the pharmaceutical composition and the kit are applicable to the method of preventing hypotension in a patient described herein.

In an embodiment, the hypotension is centrally-mediated hypotension. In an embodiment, the hypotension is peripherally-mediated hypotension. In an embodiment, the method induces metabolic depression in the patient. In an embodiment, the method prevents bradycardia in the patient. In an embodiment, the method induces metabolic depression in the patient and prevents bradycardia in the patient. In an embodiment, the method further comprises administration of a further active pharmaceutical ingredient (API) to the patient.

In one aspect, a method of preventing bradycardia in a patient is provided. The method comprises the step of administrating a pharmaceutical composition comprising i) an A1 adenosine receptor (A1AR) agonist, ii) an A1AR antagonist, and iii) an anticholinergic to the patient, wherein the administration prevents bradycardia in the patient.

The previously described embodiments of the pharmaceutical composition and the kit are applicable to the method of preventing bradycardia in a patient described herein.

In an embodiment, the method induces metabolic depression in the patient. In an embodiment, the method prevents hypotension in the patient. In an embodiment, the hypotension is centrally-mediated hypotension. In an embodiment, the hypotension is peripherally-mediated hypotension. In an embodiment, the method induces metabolic depression in the patient and prevents hypotension in the patient. In an embodiment, the hypotension is centrally-mediated hypotension. In an embodiment, the hypotension is peripherally-mediated hypotension. In an embodiment, the method further comprises administration of a further active pharmaceutical ingredient (API) to the patient.

Examples

Animal care and experiments were conducted and followed under the guidelines set forth by Guide and Use of Laboratory Animals, eighth Edition. All procedures and protocols complied with the Animal Welfare Act and were approved by the Institutional Animal Care and Use Committee (IACUC). Sprague-Dawley rats were obtained from the breeding colony of the University of Alaska Fairbanks Biological Research and Diagnostic Facility. This colony is derived from S/A Simonsen albino rats (Simonsen Laboratories, Gilroy, Calif.). Animals were housed in groups of two or more in clear polycarbonate cages (8.5"W×17"D× e8.5"H) with white spruce or pine chip bedding. Food and water were available ad libitum. The photoperiod was kept at a cycle of 12 h light to 12 h dark. Ambient temperature in the habitat was set to 21° C.

Minimizing Hemodynamic Effects

Fifteen different treatment combinations were administered to five male Sprague-Dawley rats with an average age of 314±88 days and weight of 453±44 g (mean±SD) in a modified cross over design as shown in Table 1). Not all rats were able to receive all treatments due to transmitter failure. A washout period of at least one week was allowed between treatments. One hour of baseline data (body temperature, blood pressure, heart rate, and metabolism) was acquired before treatment. Rats received either a single IP injection of CHA or were pre-treated with antagonists 15 or 30 minutes prior to CHA drugs and were then placed on a 4° C. cooled surface (previously described Laughlin et al; herein incorporated by reference). Surface temperature was manually adjusted to prevent body temperature from falling below 32° C.

TABLE 1

| Treatment | Rat 1 | Rat 2 | Rat 3 | Rat 4 | Rat 5 |
|---|---|---|---|---|---|
| CHA 1 mg/kg | X | X | X | X | X |
| CPA 1 mg/kg | X | X | X | X | |
| CHA 1 mg/kg + SPT 10 mg/kg | X | X | X | X | |
| CPA 1 mg/kg + SPT 10 mg/kg | X | X | X | X | |
| SPT 10 mg/kg 15 min before 1 mg/kg CPA + SPT 10 mg/kg | X | X | X | X | |
| SPT 25 mg/kg 15 min before 1 mg/kg CHA | X | X | X | X | |
| CHA 1 mg/kg 30 min before 25 mg/kg SPT | X | X | X | X | |
| Atropine 0.54 mg/kg 15 min before 1 mg/kg CHA | | X | | X | X |
| Atropine 1 mg/kg 15 min before 1 mg/kg CHA | | X | | X | X |
| Propranolol 4 mg/kg 30 min before 1 mg/kg CHA | | X | X | X | X |
| Diphenhydramine 4 mg/kg 30 min before 1 mg/kg CHA | | X | | X | X |
| Atropine 1 mg/kg + SPT 25 mg/kg 15 min before 1 mg/kg CHA | | X | | X | X |
| Propranolol 4 mg/kg + 25 mg/kg SPT 15 min before 1 mg/kg CHA | | X | | X | X |
| Diphenhydramine 4 mg/kg + SPT 25 mg/kg 15 min before 1 mg/kg CHA | | X | | X | X |
| Saline 1 mg/kg | | | | X | X |

8-SPT Dose Determination (IV)

Figure 1:
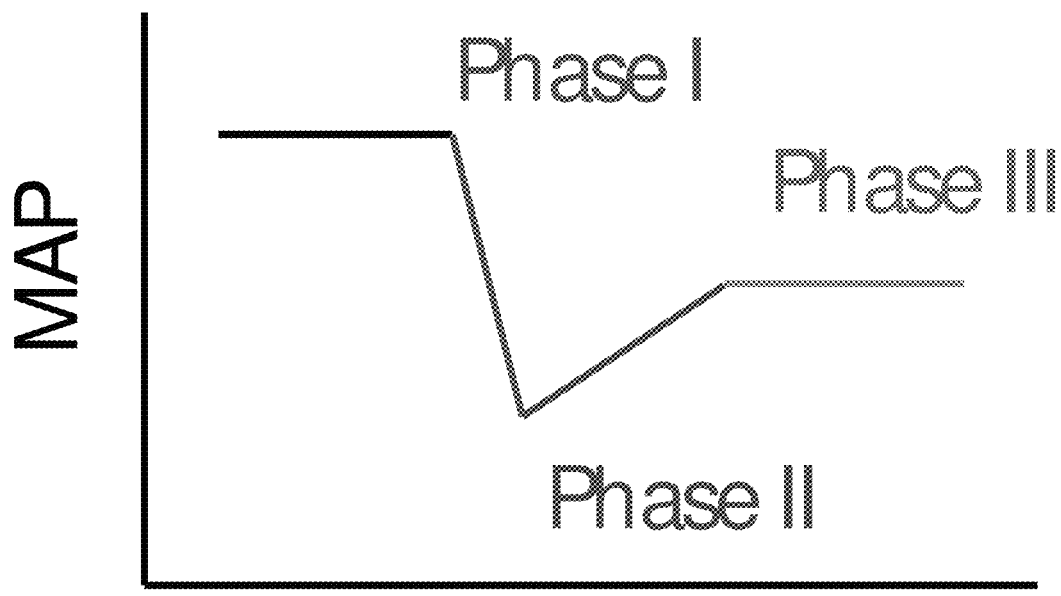
Figure 2:
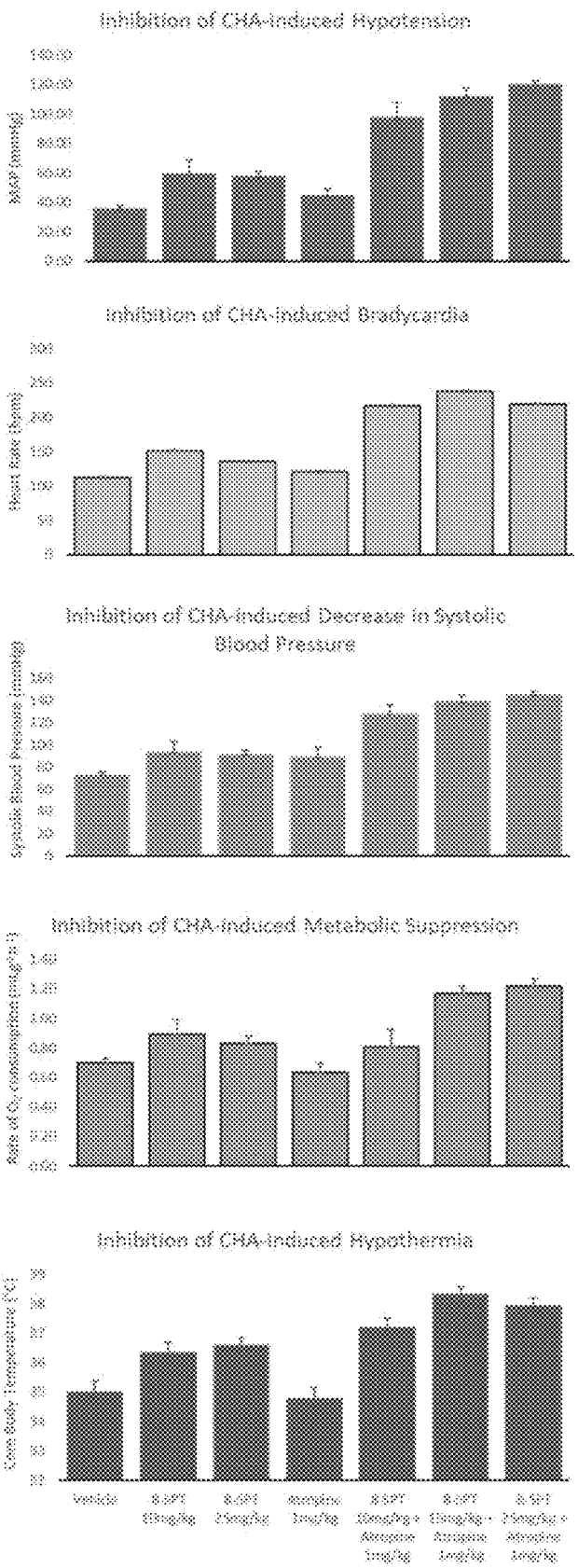
Figure 3:
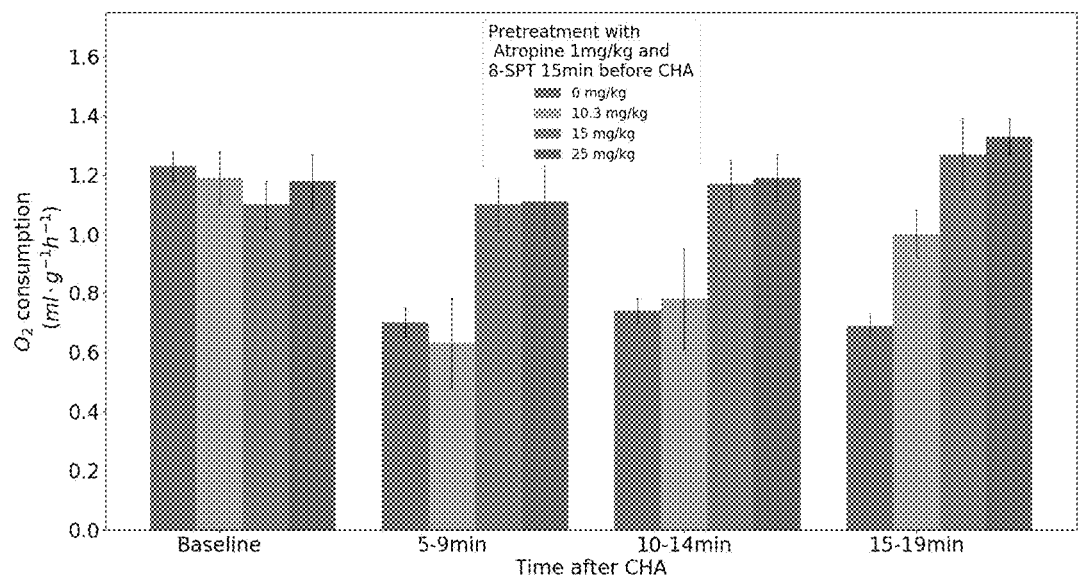
Figure 4:
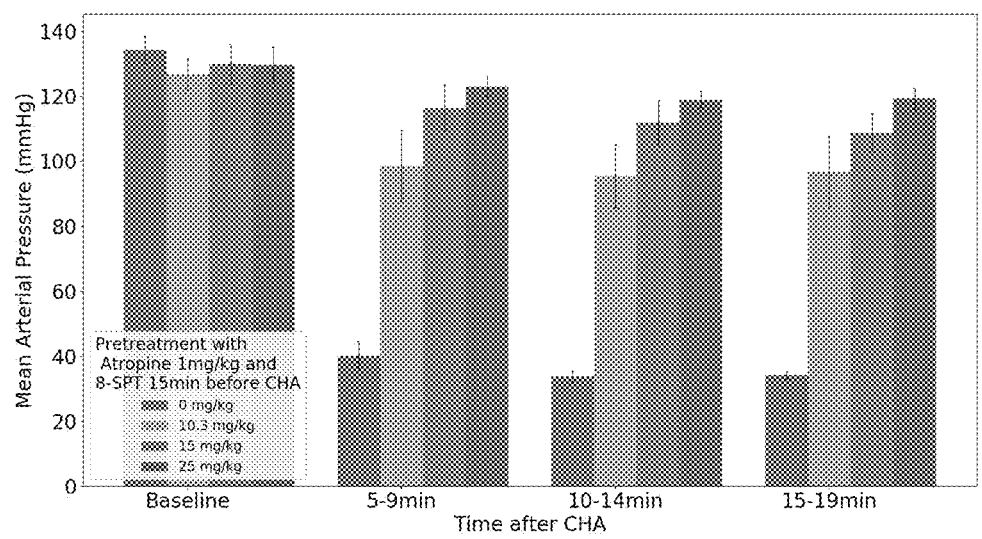
Figure 5:
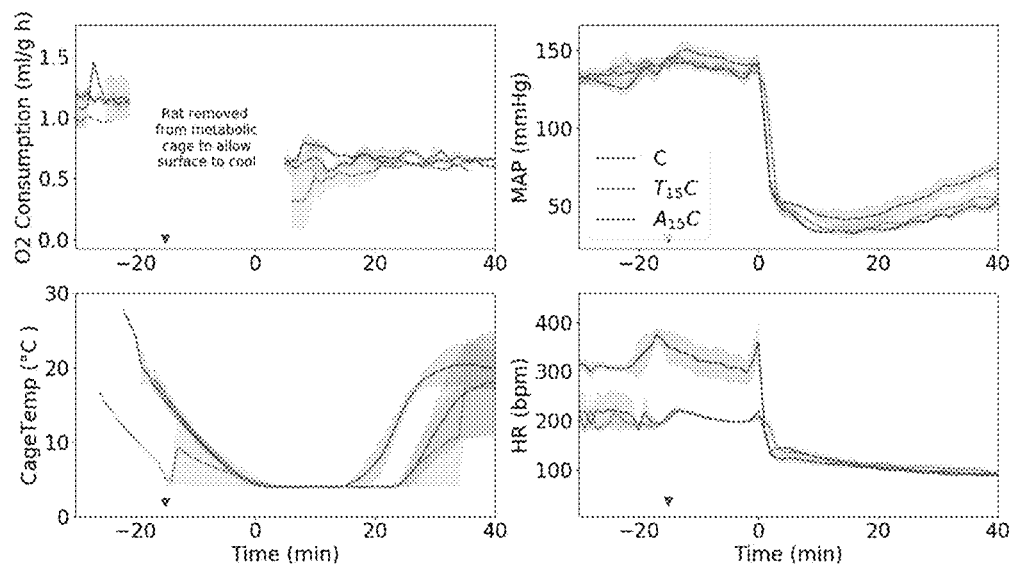
Figure 6:
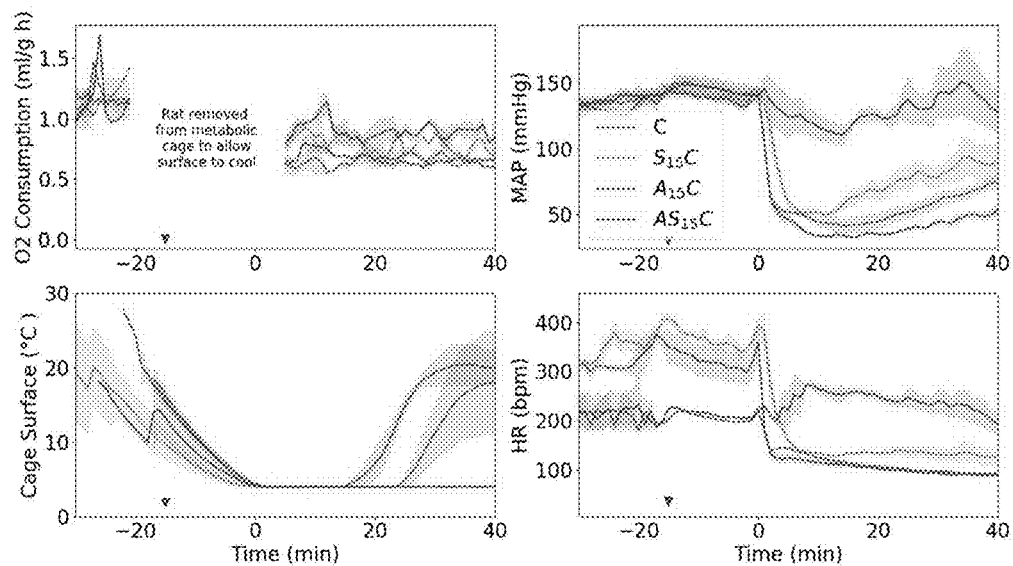
Figure 7:
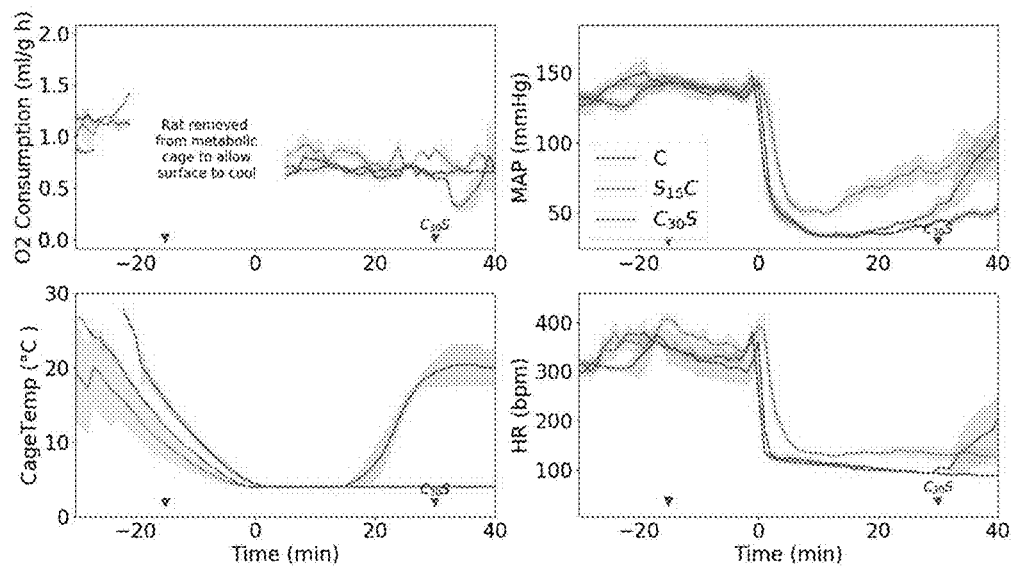
Figure 8:
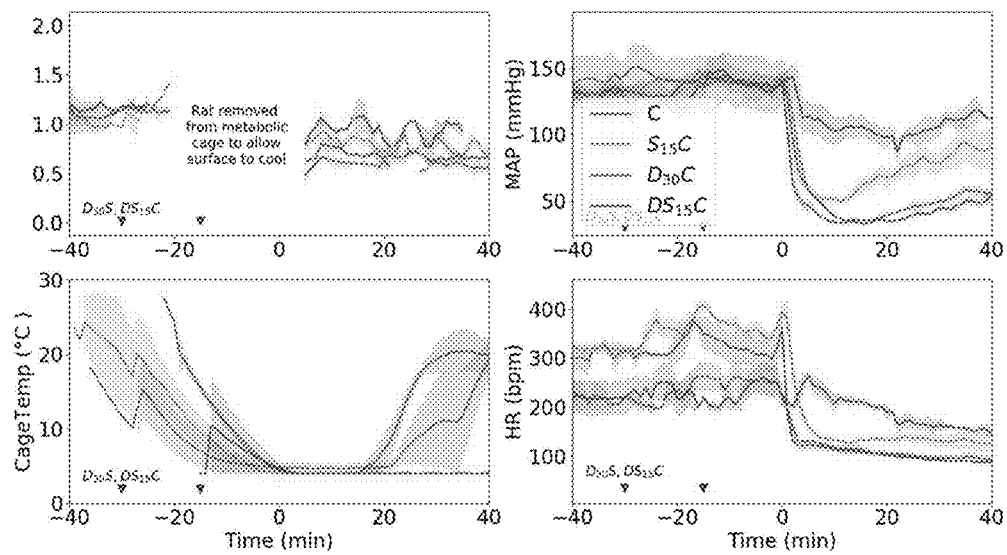
Figure 9:
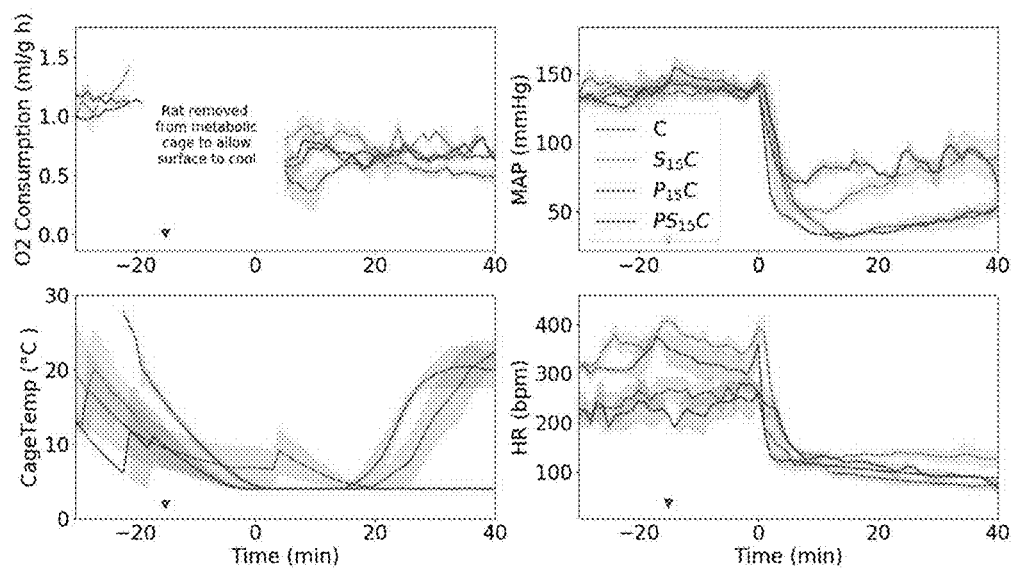
Figure 10:
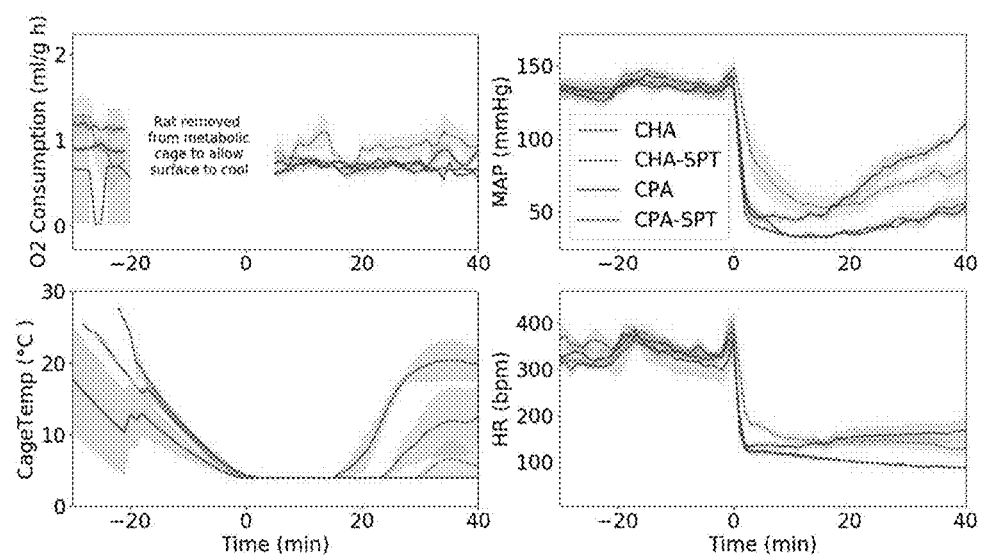

To define the dose-response relationship between 8-SPT combined with a constant concentration of atropine and CHA, three drug treatment combinations with varying doses of 8-SPT were tested. Drugs were administered to four male and one female Sprague-Dawley rat with an average age of 189±54 days and weight of 354±68 g (mean±SD) in a cross over design as described in Table 2). One hour of baseline data (body temperature, blood pressure, heart rate, and metabolism) were acquired before treatment. Rats received IV bolus of Atropine and 8-SPT 15 minutes before CHA. An IV loading dose of CHA was administered followed by a two hour continuous infusion of CHA. Rats were placed on a 4° C. cooled surface (previously described Laughlin et al). Surface temperature was manually adjusted to prevent body temperature from falling below 32° C. Results describe three phases of altered hemodynamics (FIG. 1). Results also show synergism between atropine and 8-SPT to reverse effects of CHA on mean arterial pressure (MAP), heart rate (HR), systolic blood pressure, rate of oxygen consumption (metabolic rate) and core body temperature (FIGS. 2-10).

TABLE 2

| Treatment | Rat 1 | Rat 2 | Rat 3 | Rat 4 | Rat 5 |
|---|---|---|---|---|---|
| 8-SPT 5 mg/kg + Atropine 1 mg/kg 15 min before 8-CHA 1 mg/kg | X | X | X | X | X |
| 8-SPT 10 mg/kg + Atropine 1 mg/kg 15 min before 8-CHA 1 mg/kg | X | X | X | X | X |
| 8-SPT 25 mg/kg + Atropine 1 mg/kg 15 min before 8-CHA 1 mg/kg | X | X | X | X | X |

Cardiac Arrest Treatment

The thermolytic, anticonvulsant and neuroprotective efficacy of a combination of atropine and 8-SPT followed by continuous infusion of CHA relative to standard of care (buspirone followed by continuous infusion of meperidine) was assessed. Three female and nine male Sprague-Dawley rats with an average age of 183±46 days and weight of 359±52 g (mean±SD) underwent seven minutes of asphyxia to induce cardiac arrest followed by up to two minutes of CPR to achieve ROSC. If ROSC was achieved, rats then received the following randomly allocated set of IV drugs: 1):Atropine 1 mg/kg IV bolus followed immediately with 8-SPT 25 mg/kg IV bolus and 15 minutes later CHA 1 mg/kg IV loading dose and continuous infusion at 0.25 mg/kg/hr. 2): Saline 2 mg/kg IV bolus followed immediately with Buspirone 0.064 mg/kg IV bolus and 15 minutes later Meperidine 3.6 mg/kg 1V loading dose and continuous infusion at 1.6 mg/kg/hr, and buspirone, continuous infusion at 0.02 mgkg-$^1$ h-$^1$. Treatment was started one hour (n=6) or two hours (n=6) after ROSC.

After receiving a loading dose of either CHA or Meperidine, rats were placed on a 4° C. cooled surface and continuous drug infusion was started at 2 μL/min (CMA/100, Harvard Apparatus, Holliston, Mass.). Once body temperature reached 32° C., cage surface temperature was adjusted to maintain at that level for 24 hours. After 24 hours, rats were rewarmed to 37° C. at 0.5° C./hour. Cage surface was automatically adjusted based on current body temperature, set point, error, and cooling/warming rate through a custom written python script.

Video (CAM10b, Notocord, Newark, N.J.) was acquired to capture seizure-like events and activity. Temperature and video was acquired with notochord-hem software (Notocord, Newark, N.J.). Temperature was exported to excel every minute and averaged and imported into software to adjust surface temperature.

Oxygen consumption and carbon dioxide production were acquired with open flow respirometry and imported in LabGraph (Oivind Toien, Fairbanks, Ak.). If rats were not self-feeding 24 hours after start of the experiment, they were given 1:1 chow:sugar solution (1 mL/100 g b.w.) three times per day. Neurological deficits scores (NDS((Kattz et al) were acquired daily for seven days after ROSC. Five components (consciousness and respiration, cranial nerve function, motor deficit, sensory deficit, and coordination deficit) comprise NDS. Scores range from 0 (normal) to 100 (brain dead). Initial score was obtained one or two hours after ROSC depending on treatment group.

Abdominal Transmitter Implantation and Femoral Artery and Vein Cannulation

For experiment one and two telemetry transmitters containing a pressure transducer (HD-S11, Data Sciences International, Saint Paul, Minn.) were implanted the abdominal cavity and bio-potential leads were sutured to the right pectoralis and left intercostal muscle to form a lead II ECG configuration. The pressure transducer was cannulated into the descending abdominal aorta. For experiment three telemetry transmitters (Medium and Large transmitters, Stellar-Telemetry Chesterfield, Mo.) were implanted in the abdominal cavity.

In all experiments, the femoral artery was exposed and cannulated with a 12 cm 3Fr polyurethane catheter (C30PU-RECA1302, Instech, Plymouth Meeting, Pa.), and the femoral vein was cannulated with a 10 cm 3Fr polyurethane catheter (C30PU-RJV1420, Instech, Plymouth Meeting, Pa.). A plastic trocar was used to feed the cannulae out through an interscapular incision. The cannulae were attached to a two channel vascular access button (VABR2B/22, Instech, Plymouth Meeting, Pa.). Baytril (8.88 mgkg$^{-1}$) was administered 12 hours before surgery and BID for three days post-op. Pain was managed with extended release buprenorphine (Buprenorphine SR™) 1.0 mgkg$^{-1}$ (single injection lasts 72 hours). Sutures and wound clips were removed 7-10 days post op. In order to maintain catheter patency, lines were flushed every five days with saline and filled with a heparin/glycerol locking solution (final concentration of 500 IU/mL of autoclaved USP glycerol).

Cardiac Arrest Procedure

Rats were anesthetized with 2% isoflurane with N2O flow at 1 L/min and O2 flow at 0.5 L/min. They were then intubated with a 14-gauge intravenous catheter serving as an endotracheal tube (Source of catheter). Blood pressure was monitored by a pressure transducer (BP-100, iworx, Dover, N.H.) connected to the arterial line. ECG was acquired with platinum electrodes placed in a lead II configuration. Pressure and ECG signals were recorded in Lab Scribe (iworx, Dover, N.H.). A thermocouple was placed in the rectum to approximate core body temperature and a needle thermocouple was inserted in the temporalis muscle to approximate brain temperature. Temporalis and rectal temperature was maintained between 36.5-37.5° C. via a heat lamps connected to a controller (Omega (Stamford, Conn.) T-CS32) that turned on or off lamps given temperature threshold. Rats were then administered 0.3 mL of 10 mg/mL vecuronium, IV to paralyze the diaphragm and mechanical ventilation (ugo basile, Italy) commenced with respiratory rate (RR) and tidal volume (TV) preset to individualized calculated levels based on weight (Schmidt-Nielsen).

Blood gas samples were acquired every 10 minutes (ABL90 Flex, Radiometer, Brea, Calif.) and RR, TV and N2O:O2 ratio were adjusted to meet the following requirements: pCO2 between 35-40 mmHg and O2 between 100-130 mmHg. After blood gas requirements were met, 0.3 mL of 10 mg/mL of vecuronium was administered and isoflurane was adjusted to 0%. Two minutes after lowering isoflurane the ventilator was disconnected from the endotracheal tube and the tube was plugged for seven minutes to induce asphyxia and cardiac arrest. After seven minutes, the ventilator was reattached with the RR set to 80 with 100% O2 at 2 L/min and 5 cm of PEEP. A maximum of 2 doses of epinephrine (1 mL/Kg of 5 µg/mL) IV were given separated by one minute and up to three minutes of CPR was performed. If ROSC was achieved within 3 minutes, then 0.9 mL of 8.4% sodium bicarbonate IV was administered. After 10 minutes RR, TV and O2:N20 ratio was set back to pre-arrest levels if P02 and PCO2 normalized to within (give parameters). Rats were extubated when they stated to breathe on their own. Rats were assigned to category 1 if final pCO2=35-40 mmHg and PO2=100-130 mmHg or category 2 if pCO2>50 mmHg and pO2<100 mmHg.

Active Ingredients: N6-cyclohexyladenosine, busprirone hydrochloride, and meperidine hydrochloride was purchased from Sigma-Aldrich (Saint Louis, Mo.). Sodium 8-(p-Sulfophenyl) theophylline was procured from AVISTA Pharma (East Rutherford, N.J.). CHA was dissolved in 25% (w/v) hydroxypropyl-beta-cyclodextrin (Tokyo Chemical Industry CO., Nihonbashi-honcho, Chu-Ku, Tokyo, Japan) in sterile water. Solutions for injection were sterilized by 0.2 µm filtration (Acrodisc syringe filter, Sigma-Aldrich, Saint Louis, Mo.).

Metabolic Cage with Temperature Control

Rats were placed inside a 12"×12" clear acrylic box without bedding sitting on top of a custom built, aluminum hydronic surface. The aluminum surface was part of a cooling and heating system controlled by a thermostat in which circulating water was heated or cooled via thermoelectric Peltier plates and pumped through the aluminum cage floor. This device uses circulating water as a conduction medium, similar to other commercial cooling devices. Heat conductivity of this device may be greater than the water-cooled blankets used clinically due to the high heat conductivity of aluminum. Food and water was provided ad libitum. The vascular access button was attached to a tether and swivel (Instech, VAHD115T, 375/D/22, Plymouth Meeting, Pa.) connected to a counter balance arm to provide freedom of movement.

We demonstrate that atropine 1 mg/kg along with 10 mg/kg of 8-SPT work together synergistically to mitigate the initial hypotension after CHA administration. We also demonstrate that a 10:1 ratio of CHA to 8-SPT is more effective compared to a 15:1 and 25:1 for metabolic suppression while still preventing hemodynamic side effects of hypotension and bradycardia.

Figure 11:
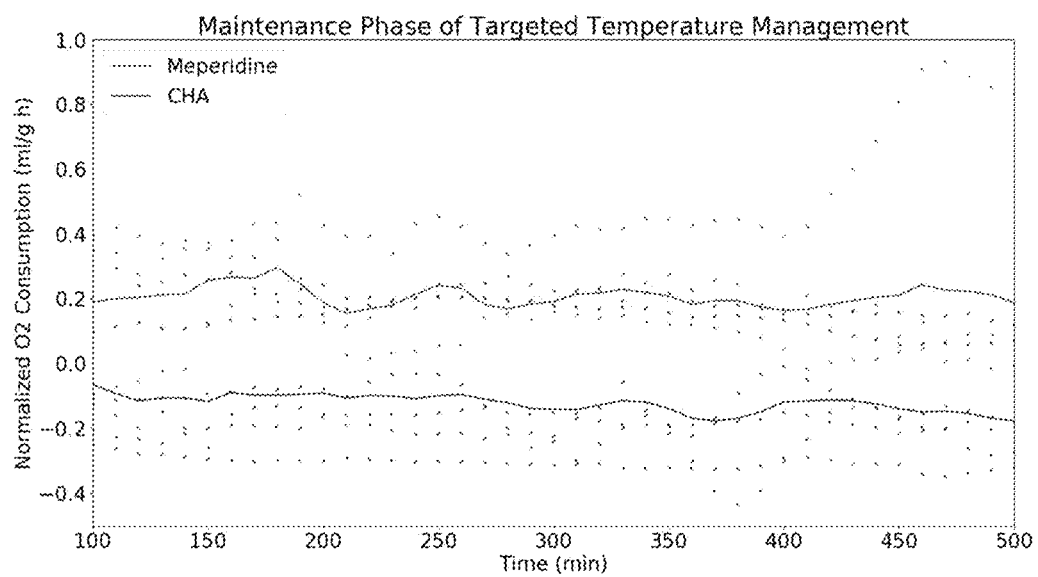
FIG. 11 shows rats treated with CHA and exposed to a 4° C. surface temperature after cardiac arrest have a lower metabolic rate compared to rats treated with meperidine and buspirone.
Figure 12:
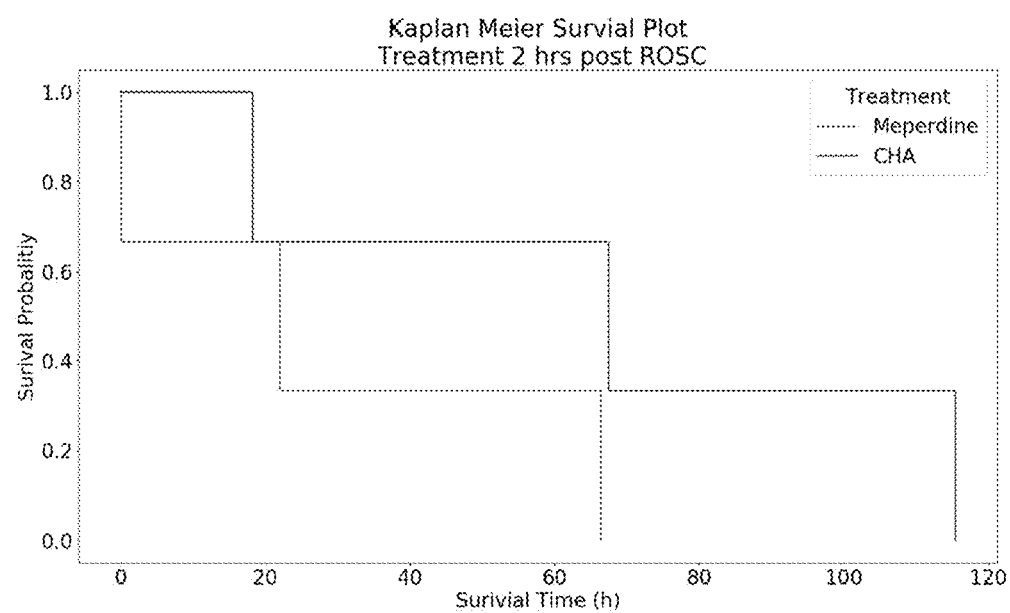
FIG. 12 shows suppressing metabolism with our CHA formulation two hours after cardiac arrest improved survival rates compared to rats treated with meperidine and buspirone.

Results show that treatment with 8-SPT, atropine and CHA (labeled in FIGS. 11-12 as CHA) results in a lower rate of oxygen consumption than treatment with meperidine and buspirone (labeled in FIG. 11-12 as Meperidine). Lower rate of oxygen consumption was also associated with enhanced survival in the rats treated with 8-SPT, atropine and CHA (labeled in FIGS. 11-12 as CHA) than in rats treated with meperidine and buspirone (labeled in FIG. 11-12 as Meperidine).

The invention claimed:

1. A pharmaceutical composition comprising i) an A1 adenosine receptor (A1AR) agonist, wherein the A1AR agonist comprises $^6$N-cyclohexyladenosine (CHA), ii) an A1AR antagonist, wherein the A1AR antagonist comprises 8-(p-sulfophenyl)theophylline (8-SPT), and iii) an anticholinergic, wherein the anticholinergic is atropine.

2. The pharmaceutical composition of claim 1, wherein the pharmaceutical composition comprises a ratio of the A1AR agonist and the A1AR antagonist (mg/kg:mg/kg).

3. The pharmaceutical composition of claim 2, wherein the ratio is selected from the group consisting of 25:1 A1AR agonist:A1AR antagonist, 24:1 A1AR agonist:A1AR antagonist, 23:1 A1AR agonist:A1AR antagonist, 22:1 A1AR agonist:A1AR antagonist, 21:1 A1AR agonist:A1AR antagonist, 20:1 A1AR agonist:A1AR antagonist, 19:1 A1AR agonist:A1AR antagonist, 18:1 A1AR agonist:A1AR antagonist, 17:1 A1AR agonist:A1AR antagonist, 16:1 A1AR agonist:A1AR antagonist, 15:1 A1AR agonist:A1AR antagonist, 14:1 A1AR agonist:A1AR antagonist, 13:1 A1AR agonist:A1AR antagonist, 12:1 A1AR agonist:A1AR antagonist, 11:1 A1AR agonist:A1AR antagonist, 10:1 A1AR agonist:A1AR antagonist, and 1:1 A1AR agonist:A1AR antagonist.

4. The pharmaceutical composition of claim 1, wherein the pharmaceutical composition comprises a ratio of the A1AR agonist, the A1AR antagonist, and the anticholinergic (mg/kg:mg/kg:mg/kg).

5. The pharmaceutical composition of claim 4, wherein the ratio is selected from the group consisting of 25:1:1 A1AR agonist:A1AR antagonist:anticholinergic, 24:1:1 A1AR agonist:A1AR antagonist:anticholinergic, 23:1:1 A1AR agonist:A1AR antagonist:anticholinergic, 22:1:1 A1AR agonist:A1AR antagonist:anticholinergic, 21:1:1 A1AR agonist:A1AR antagonist:anticholinergic, 20:1:1 A1AR agonist:A1AR antagonist:anticholinergic, 19:1:1 A1AR agonist:A1AR antagonist:anticholinergic, 18:1:1 A1AR agonist:A1AR antagonist:anticholinergic, 17:1:1 A1AR agonist:A1AR antagonist:anticholinergic, 16:1:1 A1AR agonist:A1AR antagonist:anticholinergic, 15:1:1 A1AR agonist:A1AR antagonist:anticholinergic, 14:1:1 A1AR agonist:A1AR antagonist: anticholinergic, 13:1:1 A1AR agonist:A1AR antagonist:anticholinergic, 12:1:1 A1AR agonist:A1AR antagonist:anticholinergic, 11:1:1 A1AR agonist:A1AR antagonist:anticholinergic, 10:1:1 A1AR agonist:A1AR antagonist:anticholinergic, 10:10:1 A1AR agonist:A1AR antagonist:anticholinergic, and 10:15:1 A1AR agonist:A1AR antagonist: anticholinergic.

6. The pharmaceutical composition of claim 1, wherein the pharmaceutical composition provides synergistic suppression of metabolism.

7. The pharmaceutical composition of claim 6, wherein the suppression of metabolism is present without concomitant hypotension.

8. The pharmaceutical composition of claim 2, wherein the pharmaceutical composition provides synergistic mitigation of a CHA-induced effect.

9. The pharmaceutical composition of claim 8, wherein the CHA-induced effect is selected from the group consisting of hypotension, centrally-mediated hypotension, peripherally-mediated hypotension, bradycardia, metabolic suppression, hypothermia, decreased rate of oxygen consumption (metabolic rate), and decreased mean arterial pressure (MAP).

10. A kit comprising i) an A1 adenosine receptor (A1AR) agonist, wherein the A1AR agonist comprises $^6$N-cyclohexyladenosine (CHA), ii) an A1AR antagonist, wherein the A1AR antagonist comprises 8-(p-sulfophenyl)theophylline (8-SPT), iii) an anticholinergic, wherein the anticholinergic is atropine, and iv) a pharmaceutically acceptable carrier, wherein the anticholinergic is glycopyrrolate.

11. The kit of claim 10, wherein the pharmaceutical composition comprises a ratio of the A1AR agonist, the A1AR antagonist, and the anticholinergic (mg/kg:mg/kg:mg/kg), and wherein the ratio is selected from the group consisting of 25:1:1 A1AR agonist:A1AR antagonist:anticholinergic, 24:1:1 A1AR agonist:A1AR antagonist: anticholinergic, 23:1:1 ALAR agonist:A1AR antagonist:anticholinergic, 22:1:1 A1AR agonist:A1AR antagonist: anticholinergic, 21:1:1 A1AR agonist:A1AR antagonist: anticholinergic, 20:1:1 A1AR agonist:A1AR antagonist: anticholinergic, 19:1:1 A1AR agonist:A1AR antagonist: anticholinergic, 18:1:1 A1AR agonist:A1AR antagonist: anticholinergic, 17:1:1 A1AR agonist:A1AR antagonist: anticholinergic, 16:1:1 A1AR agonist:A1AR antagonist: anticholinergic, 15:1:1 A1AR agonist:A1AR antagonist: anticholinergic, 14:1:1 A1AR agonist:A1AR antagonist: anticholinergic, 13:1:1 A1AR agonist:A1AR antagonist: anticholinergic, 12:1:1 A1AR agonist:A1AR antagonist: anticholinergic, 11:1:1 A1AR agonist:A1AR antagonist: anticholinergic, 10:1:1 A1AR agonist:A1AR antagonist: anticholinergic, 10:10:1 A1AR agonist:A1AR antagonist: anticholinergic, and 10:15:1 A1AR agonist:A1AR antagonist: anticholinergic.

12. The pharmaceutical composition of claim 7, wherein the pharmaceutical composition comprises a ratio of the A1AR agonist, the A1AR antagonist, and the anticholinergic (mg/kg:mg/kg:mg/kg), and wherein the ratio is 10:1:1 A1AR agonist:A1AR antagonist: anticholinergic.

13. The pharmaceutical composition of claim 8, wherein the pharmaceutical composition comprises a ratio of the A1AR agonist, the A1AR antagonist, and the anticholinergic (mg/kg:mg/kg:mg/kg), and wherein the ratio is selected from the group consisting of 25:1:1 A1AR agonist:A1AR antagonist:anticholinergic, 15:1:1 A1AR agonist:A1AR antagonist:anticholinergic, and 10:1:1 A1AR agonist:A1AR antagonist: anticholinergic.

14. The pharmaceutical composition of claim 9, wherein the pharmaceutical composition comprises a ratio of the A1AR agonist, the A1AR antagonist, and the anticholinergic (mg/kg:mg/kg:mg/kg), and wherein the ratio is selected from the group consisting of 25:1:1 A1AR agonist:A1AR antagonist:anticholinergic, 15:1:1 A1AR agonist:A1AR antagonist:anticholinergic, and 10:1:1 A1AR agonist:A1AR antagonist: anticholinergic.

* * * * *